(12) United States Patent
Grage et al.

(10) Patent No.: US 7,367,942 B2
(45) Date of Patent: May 6, 2008

(54) METHOD AND APPARATUS FOR TESTING BLOOD GLUCOSE IN A REVERSIBLE INFUSION LINE

(75) Inventors: Henry Grage, Alpharetta, GA (US); Paul D. Levin, Scotts Valley, CA (US)

(73) Assignee: Palco Labs, Inc., Scotts Valley, CA (US)

(*) Notice: Subject to any disclaimer, the term of this patent is extended or adjusted under 35 U.S.C. 154(b) by 27 days.

(21) Appl. No.: 11/406,973

(22) Filed: Apr. 19, 2006

(65) Prior Publication Data

US 2007/0179437 A1   Aug. 2, 2007

Related U.S. Application Data

(60) Provisional application No. 60/764,651, filed on Feb. 2, 2006, provisional application No. 60/765,851, filed on Feb. 7, 2006.

(51) Int. Cl.
    *A61B 5/00* (2006.01)
(52) U.S. Cl. .................. 600/365; 604/66
(58) Field of Classification Search ........... 600/365, 600/345, 368, 459, 466, 309, 573, 347, 310, 600/325–326; 137/223, 226, 228, 229; 604/6.05, 247, 6.01, 67, 66, 6.11, 6.1, 6.16, 604/248, 249; 422/56–57
See application file for complete search history.

(56) References Cited

U.S. PATENT DOCUMENTS

| | | | | | |
|---|---|---|---|---|---|
| 3,832,067 | A | * | 8/1974 | Kopf et al. ................ | 356/410 |
| 3,838,682 | A | * | 10/1974 | Clark et al. ................ | 600/325 |
| 3,910,256 | A | * | 10/1975 | Clark et al. ................ | 600/325 |
| 4,231,366 | A | * | 11/1980 | Schael ...................... | 604/6.05 |
| 4,535,786 | A | * | 8/1985 | Kater ....................... | 600/573 |
| 4,573,968 | A | * | 3/1986 | Parker ...................... | 604/67 |
| 4,657,529 | A | * | 4/1987 | Prince et al. ............... | 604/6.11 |
| 4,841,974 | A | * | 6/1989 | Gumbrecht et al. ......... | 600/348 |
| 5,109,850 | A | * | 5/1992 | Blanco et al. .............. | 600/368 |
| 5,165,406 | A | * | 11/1992 | Wong ....................... | 600/345 |
| 5,178,603 | A | * | 1/1993 | Prince ...................... | 604/6.01 |
| 5,206,711 | A | * | 4/1993 | Berthold et al. ............ | 356/436 |
| 5,220,920 | A | * | 6/1993 | Gharib ..................... | 600/345 |
| 5,330,634 | A | * | 7/1994 | Wong et al. ............... | 205/777.5 |
| 5,505,828 | A | * | 4/1996 | Wong et al. ............... | 205/777.5 |
| 5,758,643 | A | * | 6/1998 | Wong et al. ............... | 600/309 |
| 5,934,310 | A | * | 8/1999 | Littlehorn ................. | 137/223 |
| 5,947,911 | A | * | 9/1999 | Wong et al. ............... | 600/573 |

(Continued)

*Primary Examiner*—Charles A. Marmor, II
*Assistant Examiner*—Anita Saidi
(74) *Attorney, Agent, or Firm*—Bruce H. Johnsonbaugh

(57) ABSTRACT

An apparatus for automatically and periodically measuring a patient's blood glucose level wherein the patient has a catheter in a blood vessel and is receiving infusion fluid through the catheter. A testing unit is provided which has a main infusion channel and, in a preferred embodiment, the testing unit includes a side channel. The side channel has a restrictive cross-sectional area compared with the main infusion channel. A glucose test chamber is formed in the side channel. First and second valves are placed adjacent the test chamber in the side channel to isolate a blood sample for testing. The isolation of the sample provides more accurate blood glucose measurements than those provided by systems of the prior art. A second embodiment of the invention has an isolatable test chamber placed in the main infusion line and no side channel is utilized.

1 Claim, 26 Drawing Sheets

U.S. PATENT DOCUMENTS

| | | | |
|---|---|---|---|
| 5,976,085 A * | 11/1999 | Kimball et al. | 600/309 |
| 6,372,182 B1 * | 4/2002 | Mauro et al. | 422/56 |
| 6,780,156 B2 * | 8/2004 | Haueter et al. | 600/459 |
| 7,162,290 B1 * | 1/2007 | Levin | 600/345 |
| 2004/0019280 A1 * | 1/2004 | Waner et al. | 600/466 |
| 2006/0189858 A1 * | 8/2006 | Sterling et al. | 600/310 |
| 2006/0189925 A1 * | 8/2006 | Gable et al. | 604/66 |

* cited by examiner

METHOD AND APPARATUS FOR TESTING BLOOD GLUCOSE IN A REVERSIBLE INFUSION LINE

CROSS-REFERENCE TO RELATED APPLICATIONS

This application claims the benefit of and priority from U.S. provisional applications Ser. No. 60/764,651 filed Feb. 2, 2006 and Ser. No. 60/765,851 filed Feb. 7, 2006.

BACKGROUND AND SUMMARY OF THE INVENTION

This invention relates to blood glucose testing in critically ill patients. The need for a convenient and easily applied method of glucose monitoring in the Intensive Care Unit became evident after the landmark study of Van den Berghe and colleagues published in the Nov. 8, 2001, issue of *The New England Journal of Medicine*.

This paper demonstrated an overall reduction in ICU patient mortality of 34% when blood glucose was kept in the 80 to 110 mg per deciliter range. Samples were taken from an arterial line at 1 to 4-hour intervals and sent to the hospital lab for analysis. In the intensive therapy group, an insulin infusion was started if blood glucose exceeded 110 mg per deciliter and was adjusted to maintain normal blood glucose levels. A virtual flood of articles have since appeared and confirm improved outcomes in the treatment of various critical conditions including infection, stroke, in patients undergoing coronary bypass surgery, and in the treatment of myocardial infarction in both diabetic and non-diabetic patients. One study showed greatly improved outcomes when diabetics were monitored and treated intensively with insulin in the hospital for three days prior to undergoing coronary bypass surgery.

Intensive treatment with insulin requires knowledge of patient blood sugar levels which presently involves obtaining either an arterial or a venous blood sample or pricking the patient's finger to obtain a capillary blood sample. Blood samples are placed on a strip and read using a home-type glucose meter. All of these methods require considerable nurse or technician time. In the U.S. at present only 20 to 30% of patients in the ICU have arterial lines. Many patients, especially non-diabetics, find repeated finger sticks objectionable. Furthermore, intermittent blood samples may not be done often enough to give an accurate picture of blood sugar levels.

Optimally, patients in critical care situations should have blood glucose levels monitored several times each hour so that insulin can be given appropriately to keep blood sugar readings in the narrow range of 80-110 mg/deciliter. Presently there is no system available that accurately and conveniently measures blood sugar without taking frequent blood samples from a patient. The present invention is able to do so by withdrawing blood from a central venous line, an arterial line or a catheter in a peripheral vein. The catheterized blood vessel in any of these locations is normally used for infusion of fluids with electrolytes or various medications. The present invention also allows these lines to monitor a patient's blood sugar as often as every three minutes so that a care giver can adjust insulin dosage as required.

Attempts have been made in the past to automatically monitor blood analytes from a patient's IV line. Generally these systems have used reversal of the direction of flow in an infusion line so that blood could be pulled out of the patient's circulation at intervals, analyzed, and then re-infused back into the patient. Examples of such device are described in U.S. Pat. No. 3,910,256 to Clark, U.S. Pat. No. 4,573,968 to Parker and U.S. Pat. Nos. 5,165,406, 5,758,643 and 5,947,911 to Wong and associates.

The devices described in the above patents measure blood analytes with sensors inside the main infusion line and no attempt has been made to isolate or compartmentalize blood samples during testing. This technique, while successful for monitoring blood gases, has not yet met with success in testing for blood glucose. The present invention, by novel means, allows practical and accurate monitoring of blood sugar from a reversible infusion line.

State of the art blood glucose measuring systems generally employ the enzymes glucose oxidase or glucose dehydrogenase. In the chemical reaction which occurs using either of these two enzymes, glucose is consumed and the electrons generated are drawn off and measured. Plotting current flow against time produces a curve which is distinctive for each glucose value, i.e., any given concentration level of blood glucose.

Accuracy depends crucially on maintaining a constant diffusion gradient over the glucose sensor. In the ideal case the concentration of glucose varies in a regular and linear way from the body's reservoir of blood glucose to the area just over the sensor where concentration drops to a minimum (close to zero) because it is being consumed in the chemical reaction. The major cause of inaccuracy in electrochemical glucose measurement is disturbance of the diffusion gradient. The problem is relatively small in single use disposable strips because a portion of a blood drop is allowed to rest undisturbed in a small channel during the test, having been drawn up into the channel by capillary attraction. In a flow-through system the problem of leaving the diffusion gradient undisturbed is a major one because of the much larger volume of fluid involved, which is essentially all the fluid in the infusion line from the patient to the bedside monitor.

A disturbance anywhere in this large reservoir of fluid is immediately transmitted to the test area and causes disturbance of the diffusion gradient over the sensing electrode. Invariably, the effect is to bring more glucose to the region of the electrode, causing an increase in the glucose signal and an overestimation of blood glucose.

A number of causes can contribute to disruption of the diffusion gradient in a flow through system. Any fluid movement, even a flow rate as low as 150 micro liters/minute, can cause a mixing effect which disturbs the diffusion gradient and gives an overestimation of blood glucose. Eddies in the fluid line can occur because of the intermittent "push" of a peristaltic pump. Such eddies can last several seconds after pumping has stopped.

Adjustment of blood temperature to ambient temperature can cause micro fluidic deviations which will disturb the diffusion gradient. Heat transfer issues are minimized by keeping the amount of fluid small in comparison to the total mass of the device. The device can be subjected to temperature controls but under practical conditions small volumes are required to prevent temperature differences from causing significant measurement errors. The diffusion gradient over the sensor can also be disturbed in an open-flow system by movement of the arm or chest, or changes in the relative position of the test chamber and the heart. Additionally, impacts to the tubing or glucose test area can cause measurement inaccuracies if the fluid in the test area is not protected in a small, well defined space.

For complete isolation, small valves, which may be inflatable balloons, can be located adjacent the test chamber. Besides protecting the diffusion gradient, isolation of the test sample prevents movement of glucose molecules into or out of the test area and allows consistent measurement of the current produced during the reaction at any given glucose level.

In the present invention, the test chamber for testing blood glucose can either be part of the main infusion line inside the testing unit, or it can be located in a side channel in the testing unit in continuity with the main channel. In the latter version, a valve, which may be an inflatable balloon, directs blood or fluid into the side channel at the time of testing. For reasons to be enumerated, the side channel version is considered the preferred embodiment of the invention.

The system to be described uses a bedside monitor with a digital readout and alarms and contains two peristaltic pumps, one of which normally infuses fluid through the blood vessel catheter. During glucose testing the pump assists in moving blood samples into and out of the test chamber. The second peristaltic pump automatically calibrates the sensor at intervals with a premixed calibration fluid.

The disposable, single patient use testing unit is approximately 2¼"×1½"×¾" and is attached to the patient's chest for use with a central line or to an extremity for use with a catheter in a peripheral vessel. The distal end of the testing unit has an integral Luer fitting which connects to the patient's blood vessel catheter. The proximal end of the testing unit has the exit sites for the fluid, air, and electric lines that connect to a bedside monitor located a few meters from the patient.

The disposable testing unit portion of the invention is made of a semi-transparent plastic. It contains a channel for infusion fluid in continuity with (i.e. in fluid communication with) the infusion line and with the blood vessel catheter. A glucose sensing electrode is located in the test chamber area of the testing unit. Chambers for inflatable balloons, which serve as valves, are molded into the plastic parts along with grooves for the air lines and the electric cable. After insertion of the various components during manufacturing, the top and bottom halves are welded together to form a leak proof disposable testing unit. While inflatable balloons are considered the preferred embodiment for reasons of economy and ease of insertion, mechanical valves can also be used for this application.

The sensor of the present invention can be automatically calibrated at selected intervals using a small bag of premixed calibration fluid which is supplied with each disposable testing unit. The calibration fluid is carried inside the monitor and made to flow through the test chamber at intervals by a second peristaltic pump. After calibration is complete the test chamber is cleared by a brief flow of infusion fluid through the sampling area.

The area of the glucose sensor in the present invention is approximately 25 square millimeters, considerably larger than that of a typical disposable strip. The height of the test chamber's is from 0.3 to 0.5 mm, giving a fluid volume in the chamber of 8 to 12 micro liters. The large electrode described herein is thought advantageous in this specific application because of the large amount of current produced during a test. Current from a 25 sq. millimeter sensor will be measured in micro amps rather than the nano amps of some single use strips. A large current flow is advantageous for optimum resolution of the signal.

In the present invention, the openings into the test chamber are at least 300 microns in height, which duplicate the height of the test chamber. Blood is quite viscous and this minimum height is necessary to allow adequate blood flow in and out of the test chamber. Positive pressure is still required to bring blood or fluid into the test chamber and for the same reason pressure is needed to clear the site once the test has been performed. The present invention is capable of exerting adequate pressure to draw in the sample or flush it from the test chamber.

In the descriptions and drawings to follow, two embodiments of the invention are shown. The first embodiment has its test chamber located directly in the main infusion line. The second embodiment has the test chamber located in a side channel, in continuity with the main channel. Several advantages accrue to the side channel version. Firstly, an unrestricted main channel (used together with a restricted side channel) allows for the rapid flow of fluid through the device most of the time. Secondly, a constant flow of fluid through the test chamber (if no side channel is used) could disperse the reagents necessary for repeated testing of blood glucose. This problem is avoided, in the preferred embodiment, since infusion fluid usually flows through the main channel. Thirdly, in the non-side channel version, a large volume of blood must be forced through the test chamber so that an undiluted sample is adjacent the sensor. Damage to red cells can occur when forcing a large quantity of blood through a very small opening. By contrast, in the side channel version blood can be easily withdrawn from the patient through the unobstructed main channel until a pure sample is opposite the test site. At that time only a very small quantity of blood need be directed into the side channel for testing.

It should be emphasized that a controllable valve in the main channel is an essential aspect of the side channel version of the invention. Without controlled blockage of the main channel, blood and fluids would always take the path of least resistance through the main channel and never enter the side channel.

In the following description of the present invention, the one or more valves inside the device are comprised of inflatable balloons. It is to be understood that mechanical valves of various types could also be used in this application. Inflatable balloons are considered the preferred embodiment for reasons of economy and for ease of insertion during assembly.

In the examples to follow, traditional monitoring in an open-flow system is compared to testing with the preferred embodiment of the present invention. Monitoring blood sugar in a conventional flow-through system is possible if there is no disturbance of the diffusion gradient over the sensing electrode. In reality, such disturbances occur constantly for the several reasons mentioned. In a flow-through system in which blood or fluid is propelled by a peristaltic pump, the cog-wheel effect is very evident and causes confusing variations to the glucose diffusion gradient. Additionally, a peristaltic flow-through system is subject to all the additional artifacts contributed by impacts to the infusion bag, the tubing and the sensor itself. Clearly a sensor which isolates the test fluid and keeps it completely at rest is best able to maintain a stable diffusion gradient and give the most accurate estimation of blood glucose.

No references in the prior art have been found to methods of isolating small extra corporal samples for testing. Therasense U.S. Pat. No. 6,120,676 states that a sensor for blood glucose can be used in a flowing sample stream which is made to flow through a sampling chamber. No method is described of sample isolation although the authors state that the sample can be made to flow at a slow rate. In claim 32 of the same patent the authors mention holding the sample stationary in a sampling chamber but the latter is on a disposable strip and not in a reversible infusion line where the sensor must test repeatedly over a period of days.

An advantage of the present invention is to put blood in contact with the sensor only briefly during each test. Following the test, the test chamber in the testing unit is flushed with clear fluid which reduces protein and fibrin deposition on the sensing membrane. For example, if a glucose test takes 20 seconds and readings are done every five minutes, then blood will be in contact with the sensor only about 3% of the total elapsed time.

A primary object of the invention is to provide a system for repeated monitoring of blood glucose from an ordinary infusion line with an accuracy approaching that of a clinical lab.

A further object of the invention is to attain such accuracy by isolation of the test sample during a test.

A further object of the invention is a system usable with equal ease in either a peripheral vein or a central venous line.

A further object of the invention is to provide a small disposable testing unit which is attachable to either the chest for proximity to a central line or to an extremity for use with a peripheral vein.

A further object of the invention is to provide a system which is automatically and periodically self-calibrating.

Other objects and advantages of the invention will become apparent from the following description and drawings.

BRIEF DESCRIPTION OF THE DRAWINGS

in FIG. 8 the balloon valves are closed and the infusion pump is reversed drawing blood backwardly through the testing unit;

FIG. 11 is a cross-sectional plan view of the second embodiment incorporating a side channel in the testing unit, shown approximately actual size;

FIG. 12 is the same schematic and plan view of FIG. 11 shown approximately twice actual size for clarity; as shown in FIG. 12, infusion fluid is flowing through the main infusion line towards the catheter in the patient's blood vessel;

FIG. 13 illustrates the infusion pump operating in the reverse or backward direction and causing blood to flow backwardly through the testing unit through the main infusion channel, with the balloon valve in the main infusion channel in its open position;

FIG. 14 shows the balloon valve in the main channel closed, thereby causing blood to be pumped by the infusion pump through the side channel and wherein the balloon valves adjacent the test chamber are opened to allow blood to fill the test chamber;

FIG. 15 shows the testing unit when the glucose level is actually being tested, wherein the balloons adjacent the test chamber are closed and isolate the blood sample;

FIG. 16 shows the flushing of the main channel shortly after the test has been performed in the test chamber wherein the balloon valve in the main channel is opened and infusion fluid is being pumped through the main channel toward the patient;

FIG. 17 illustrates the flushing or cleansing of the test chamber with calibration fluid, showing the valves adjacent the test chamber opened and the valve controlling calibration fluid opened and the valve in the main infusion channel is closed to force the calibration fluid to flow through and flush the test chamber;

FIG. 18 illustrates all four balloon valves closed after the test chamber has been flushed with calibration fluid, allowing the test chamber to be recalibrated;

FIG. 19 illustrates the reintroduction of infusion fluid through the side channel after the calibration fluid has been pumped through the side channel for calibration purposes;

FIG. 20 illustrates reintroduction of infusion fluid through the main channel;

FIG. 21 illustrates glucose consumption curves under ideal conditions utilizing a stabilized diffusion gradient according to the invention for five different blood glucose concentration levels;

FIG. 22 is a glucose consumption curve (or current flow curve) utilizing the stable diffusion gradient technique of the present invention for one given blood glucose level;

FIG. 23 illustrates a prior art glucose consumption curve wherein perturbations or disturbances caused by coughing or other chest motion of the patient will produce an erroneously high blood glucose reading;

FIG. 24 illustrates a glucose consumption curve or current flow curve where the isolation techniques of the present invention are utilized and wherein coughing or chest motion of the patient has very little, if any, effect on the blood glucose measurement;

FIG. 25 is a pair of glucose consumption curves illustrating how a slow flow rate of blood through a non-isolated prior art test chamber still produces an erroneously high blood glucose measurement.

DETAILED DESCRIPTION OF THE DRAWINGS

Figure 1:
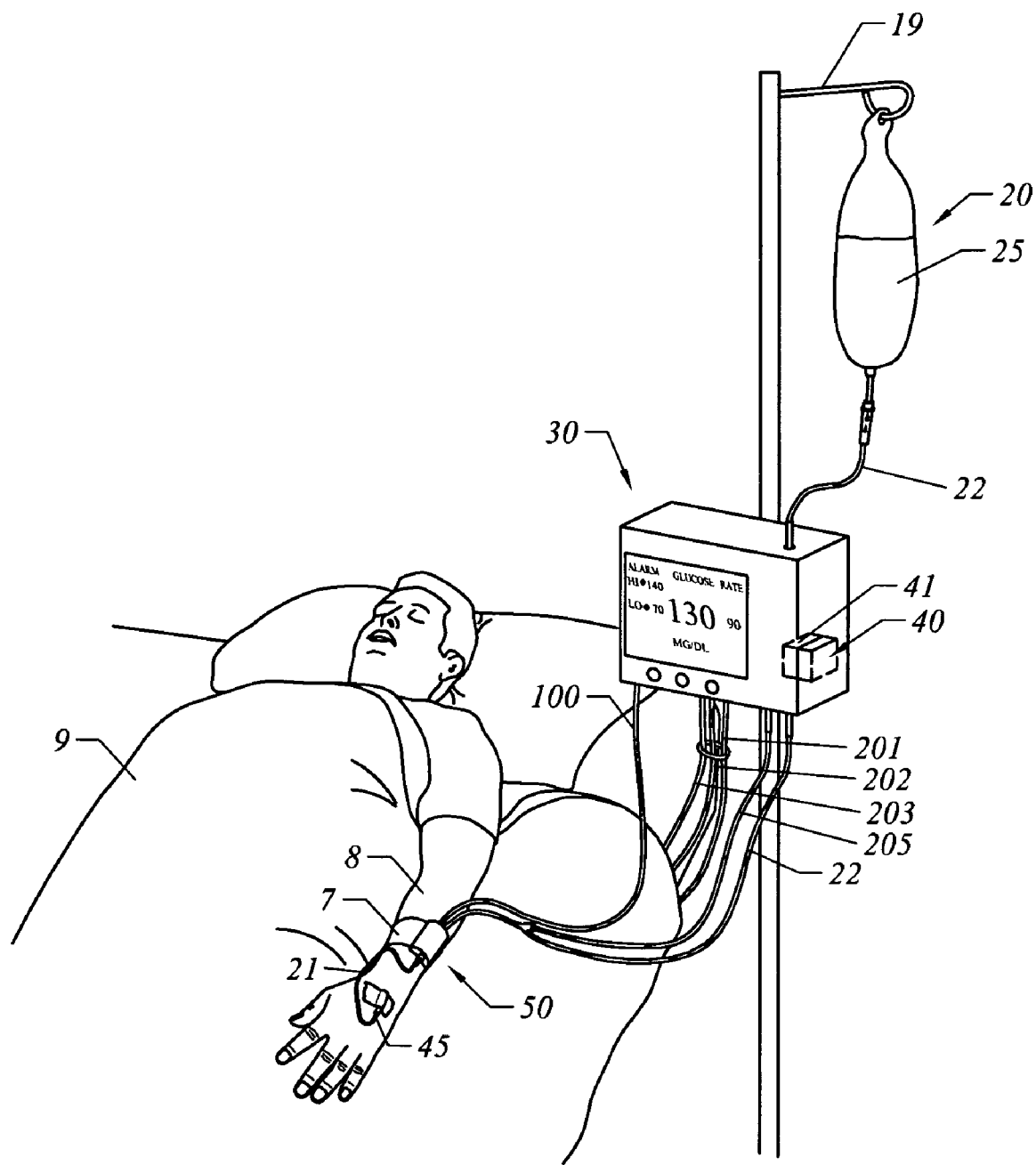
FIG. 1 is an overall view of the present invention used in conjunction with a patient.
Figure 2:
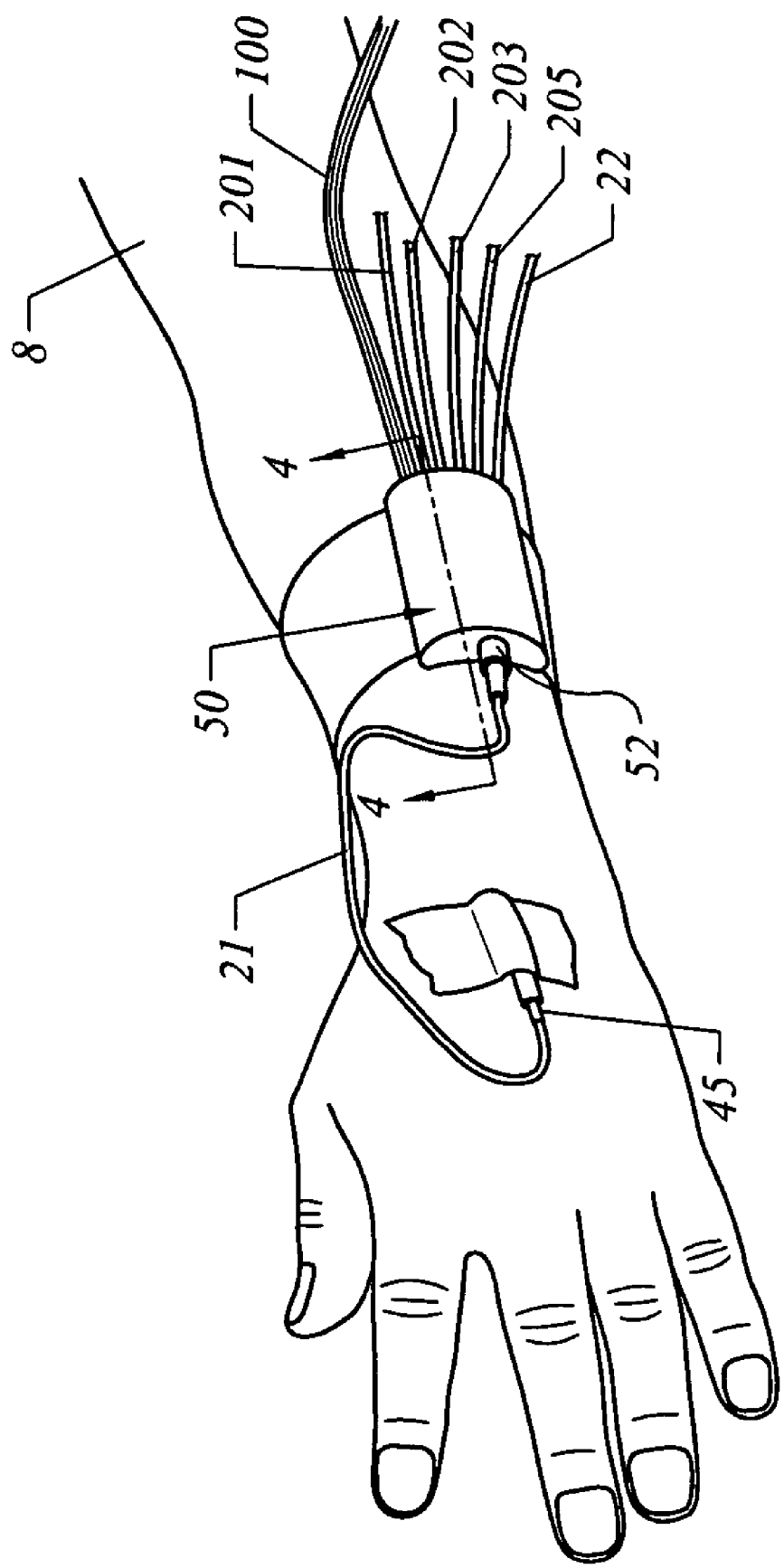
FIG. 2 is a perspective view of the disposable testing unit of the present invention attached to a patient's forearm.
Figure 3:
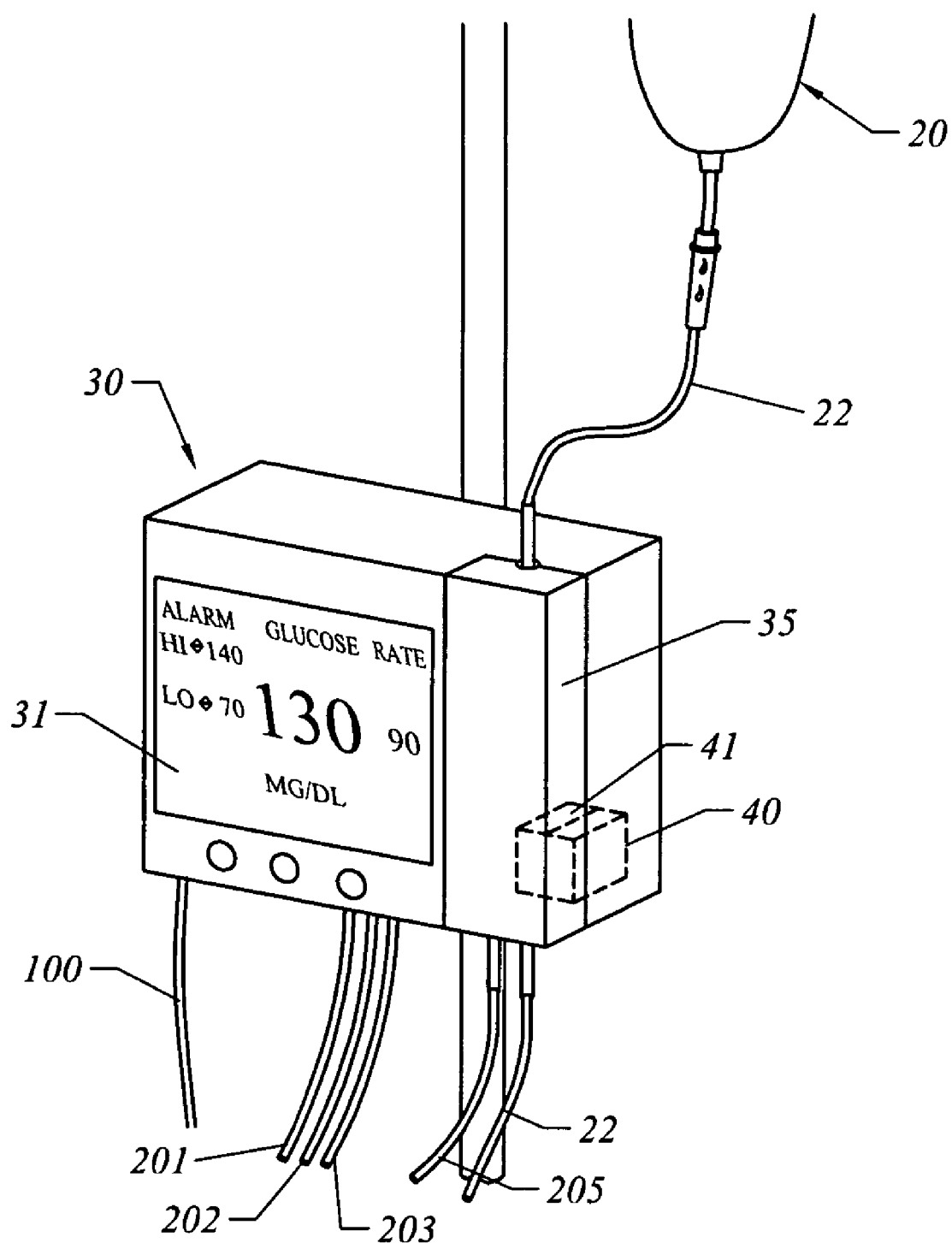
FIG. 3 is a close-up view of the bedside monitor showing the various leads and attachments.

FIGS. 1, 2 and 3 illustrate the overall environment of the invention. A hospitalized patient 9 typically in an ICU unit is shown with a disposable testing unit 50 of the present invention attached to forearm 8 by a Coban elastic band 7. A catheter 45 is shown inserted into a patient blood vessel on the back of the patient's hand. A first infusion line 21 connects catheter 45 to testing unit 50. A source of infusion fluid is shown as IV bag 20 suspended from a support 19 as is known in the art. Infusion fluid 25 stored in infusion bag 20 passes downwardly through a second infusion line 22 and through a reversible peristaltic pump 40 carried in monitor housing 30. The second infusion line 22 continues downwardly from peristaltic pump 41 and enters the test unit 50. The infusion fluid passes through testing unit 50 as described in detail below and through first infusion line 21 that extends from testing unit 50 to catheter 45 and provides infusion fluid into the patient's blood vessel. When the reversible peristaltic pump 40 is operating in its ordinary forward mode infusion fluid 21 from source 20 is pumped through infusion line 22 and through testing unit 50 and then through the lower connector 52 which attaches to IV catheter 45. When the peristaltic pump is reversed and pumps infusion fluid and blood backwardly through attached unit 50 an undiluted blood sample becomes available for testing. The presence of an undiluted blood sample is preferably determined by the optical method described in U.S. patent application Ser. No. 11/228,827 filed on Sep. 16, 2005, incorporated herein by reference. Electrical power is fed to testing unit 50 by line 100 extending from monitor 30.

Air lines 201, 202 and 203 are shown here as separate lines but in actuality are part of a triple-lumen tube which is permanently embedded in the proximal end of the testing unit 50 but attachable to the monitor 30 at the time of set-up. These lines carry air from motor-driven precision syringes to inflate or deflate small balloon valves inside the testing unit 50. Three air lines suffice when four balloons are used in the disposable testing unit 50 because two balloons adjacent the sensing chamber are always inflated or deflated at the same time.

A bag of pre-mixed calibration fluid (not shown) is situated inside the monitor and a second fluid line 205 runs from the calibration fluid bag over a second peristaltic pump 41 to reach the testing unit 50 near the entrance of main infusion line 22. Monitor 30 has a screen 31 that displays the blood glucose level from the most recent test. An access door 35 located adjacent to screen 31 opens to allow access to both peristaltic pumps (shown in phantom), replacement or removal of the infusion and calibration lines along with the bag of pre-mixed calibration fluid.

FIGS. 4-10 illustrate a first embodiment of the invention, wherein the testing unit 50 has a single main infusion passageway and no side channel.

Figure 4:
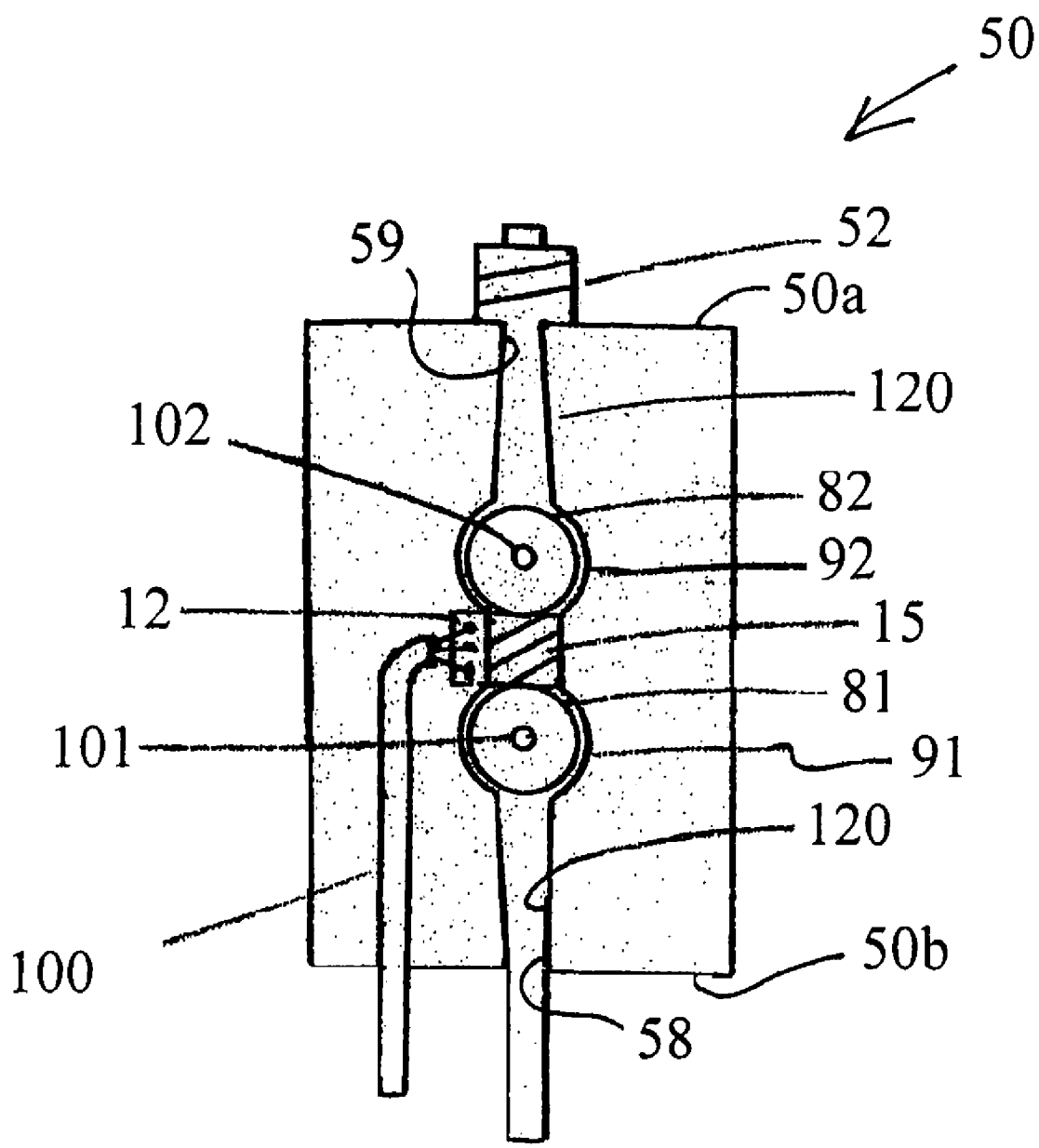
FIG. 4 is a cross-sectional plan view of a first embodiment of the disposable testing unit shown actual size.

FIG. 4 is a schematic sectional view along the line 4-4 of FIG. 2. The Luer connector 52 is permanently attached to the distal end 50a of the testing unit 50 and is in continuity with infusion channel 120. Narrow slits 58 and 59 are approximately 300 microns high and 5 millimeters wide open to the proximal and distal portions of the main channel 120. Glucose sensor 12 rests on the bottom of test chamber 15 which holds fluid for testing. Dimensions of the test chamber 15 are 5 mm×5 mm×300 microns. Sensor 12 is connected by cable 100 to the electronics of the bed side monitor 30. First and second valves 81 and 82 are situated in the main infusion line 120 and rest in balloon chambers 91 and 92.

Figure 5:
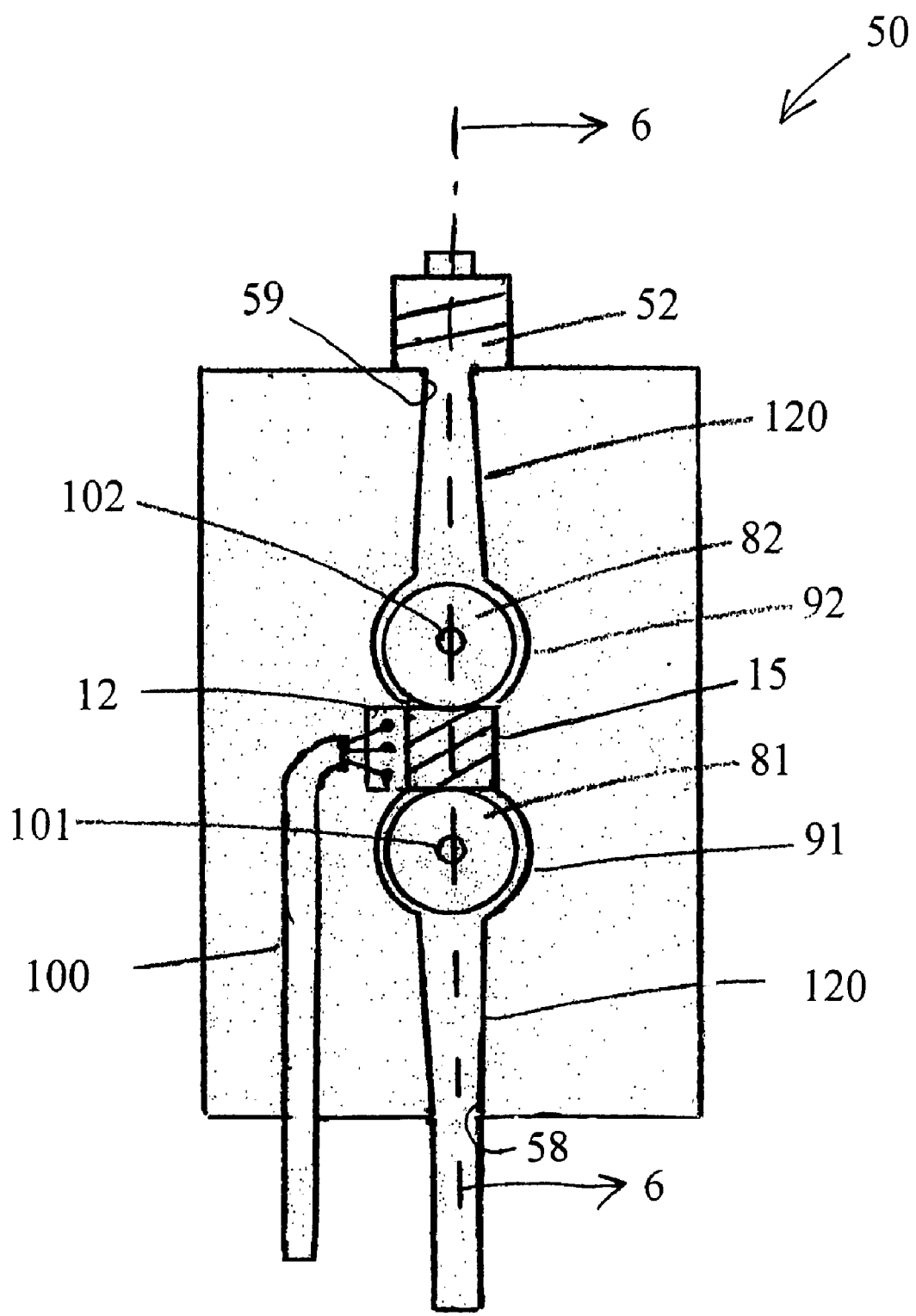
FIG. 5 is the same view as shown in FIG. 4 but expanded to twice actual size for clarity.

FIG. 5 is simply an enlargement of FIG. 4 to twice actual size for clarity.

Figure 6:
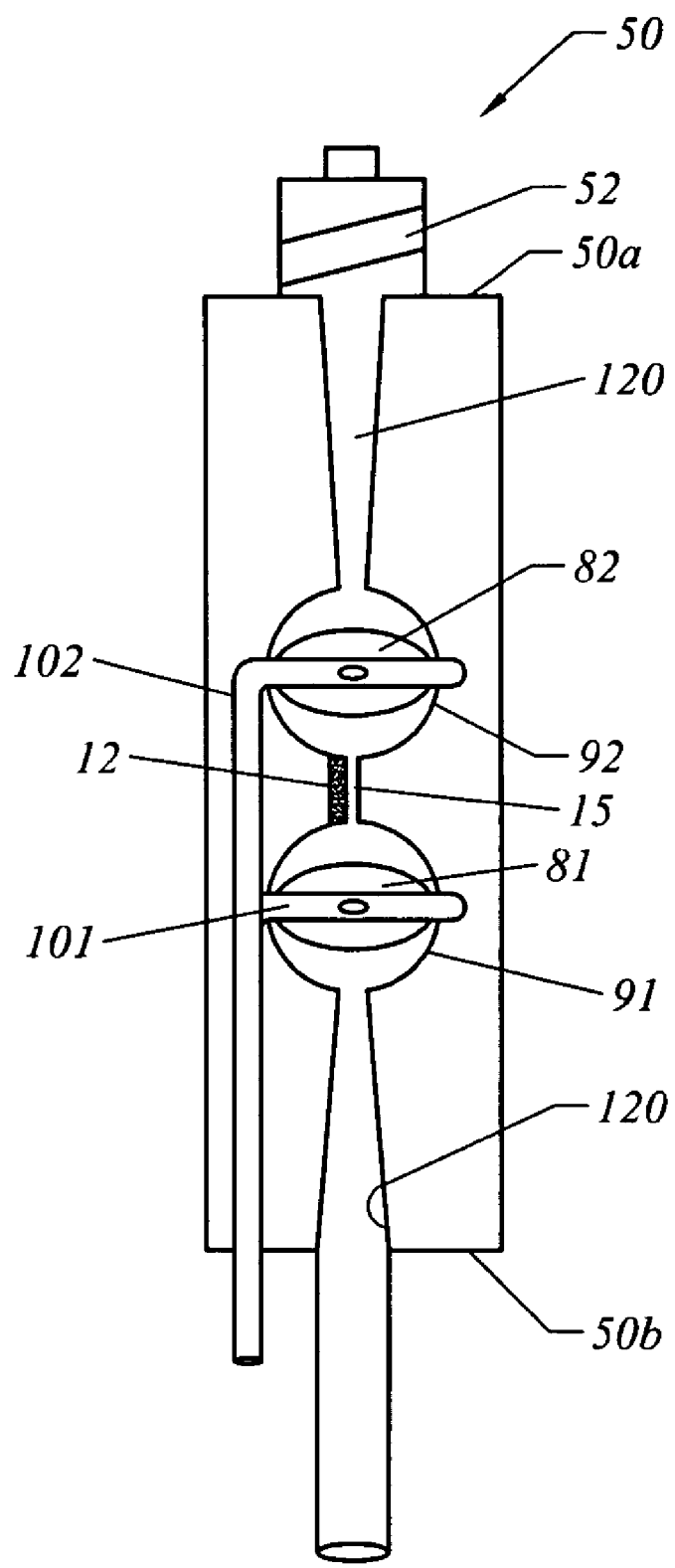
FIG. 6 is a cross-sectional view on the line 6-6 of FIG. 5; balloon valves adjacent the reaction chamber are partially inflated.

FIG. 6 is a sectional view on the line 6-6 of FIG. 5. The inflatable balloon valves 81 and 82 are shown partially inflated. Small diameter catheters 101 and 102 enter balloon chambers 91 and 92 transversely to main infusion line 120 and then make a right angle turn to exit at the proximal end 50b of the testing unit 50.

Figure 7:
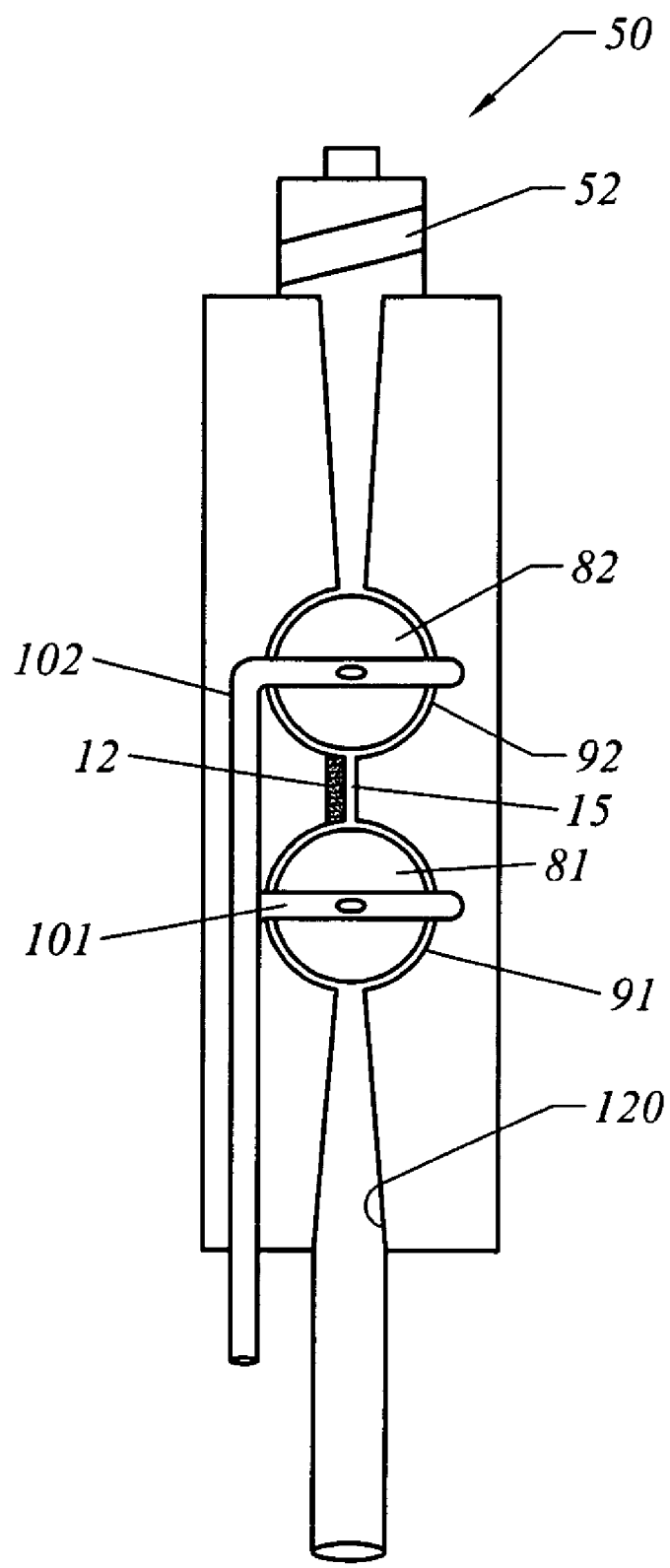
FIG. 7 is the same view as FIG. 6 with balloon valves fully inflated.

FIG. 7 is the same view as FIG. 6 but now shows the balloon valves 81 and 82 fully inflated to block the entrances to the test chamber 15. While for clarity a small space is drawn between the balloon and the balloon chamber's inner wall, in reality the balloon is under sufficient pressure to be tightly applied to the chamber wall in order to block all fluid movement.

Figure 8:
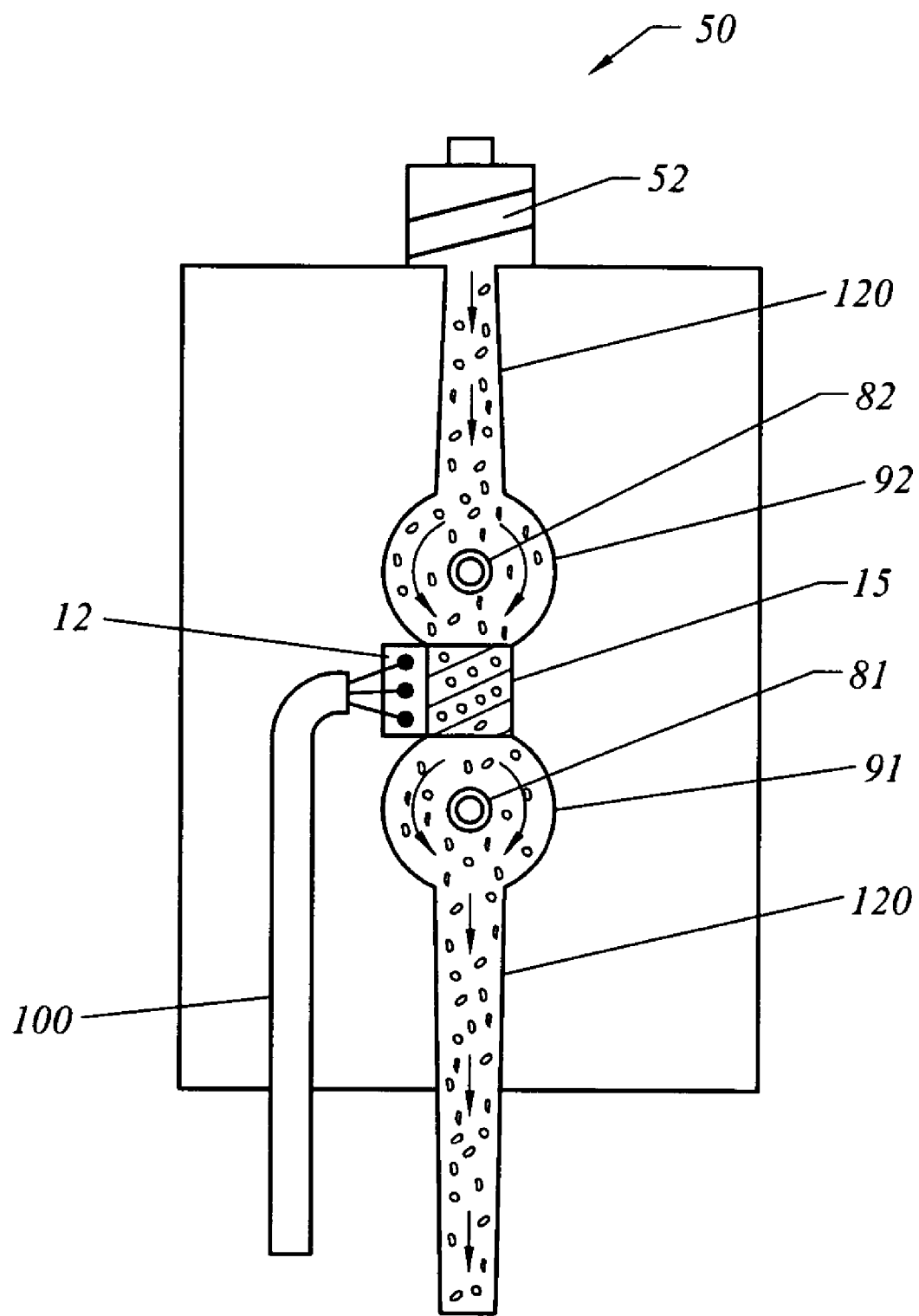
FIG. 8 is a schematic illustration of the first step of obtaining a blood sample using the device shown in FIGS. 5-7.
Figure 9:
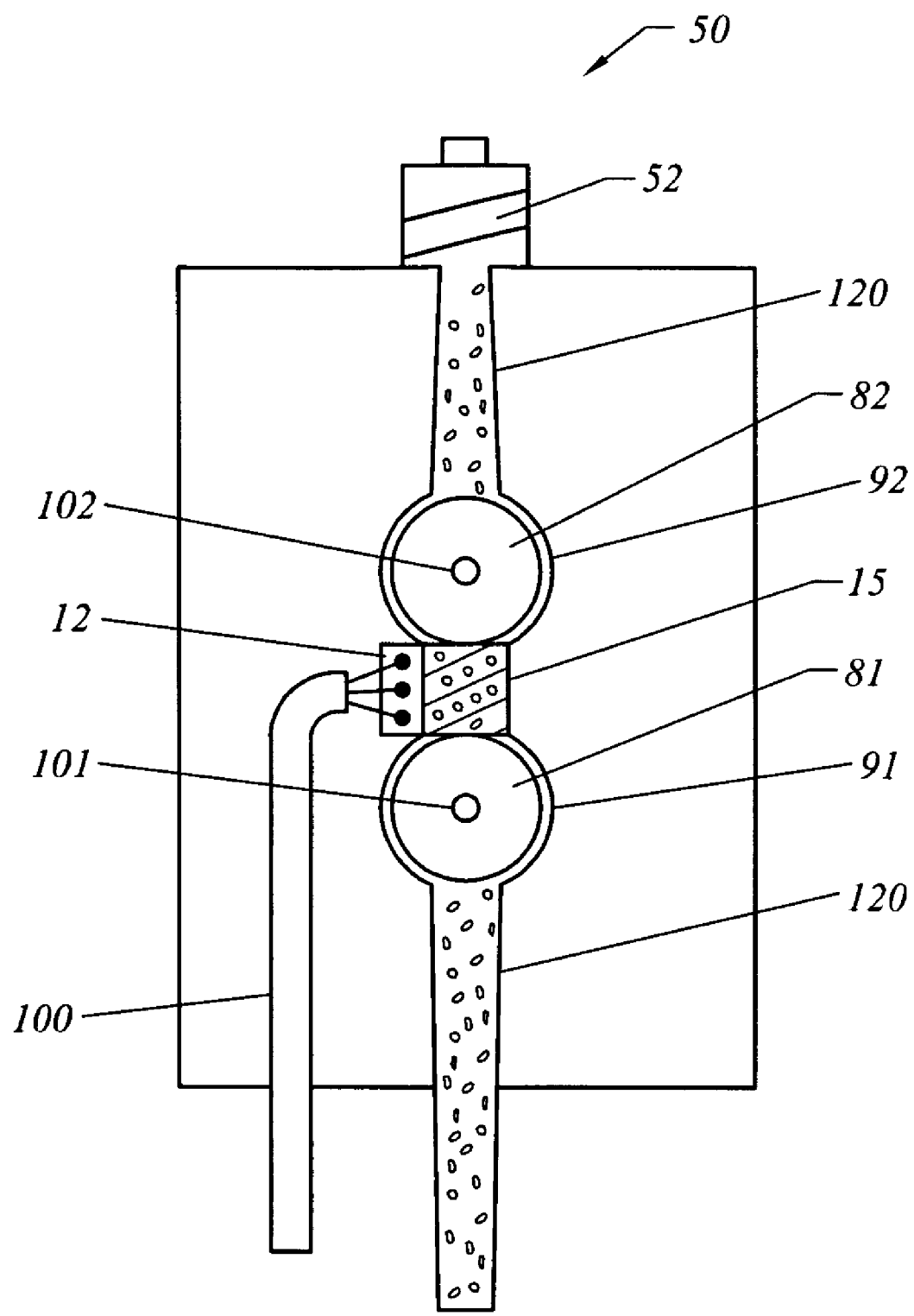
FIG. 9 is a schematic showing the second step of the process wherein the balloon valves are closed and the blood sample in the test chamber is being tested for glucose levels.
Figure 10:
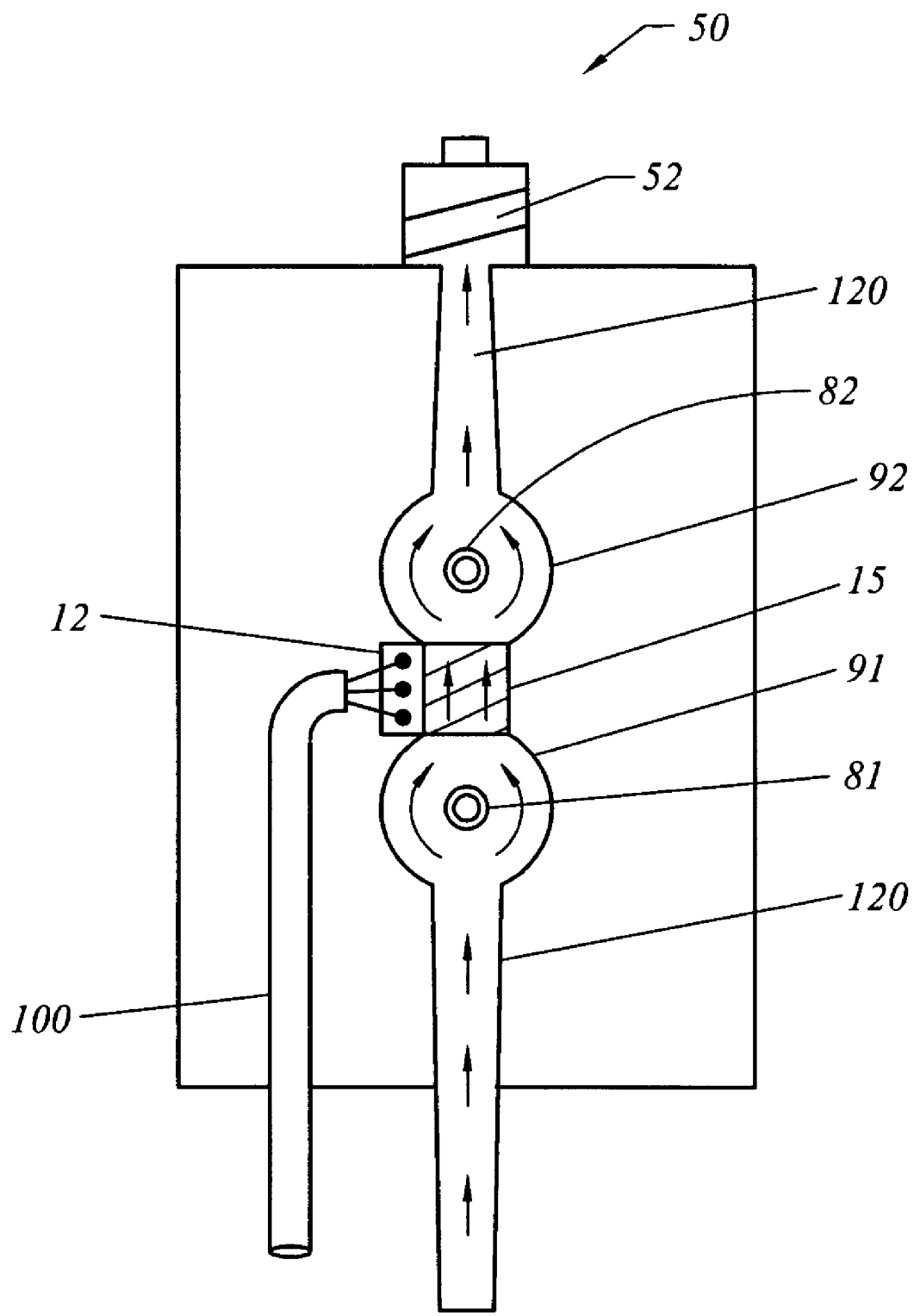
FIG. 10 shows the next step in the process wherein the balloon valves are opened and the peristaltic pump is pumping infusion fluid through the test chamber.

FIGS. 8, 9 and 10 are schematic views similar to FIGS. 4 and 5 showing operation of the first embodiment of the invention when testing for glucose. In FIG. 8, peristaltic flow has been reversed to withdraw blood from a patient. When it has been determined that a pure sample of blood is in contact with the glucose electrode 12, the peristaltic pump is stopped and balloons 81 and 82 are inflated, as shown in FIG. 9, and a measurement is taken. It is significant to note that, as shown in FIG. 9, first and second balloon valve 81,82 are adjacent test chamber 15 and on opposite sides of test chamber 15. The blood sample in test chamber 15 (and test chamber 15 itself), as shown in FIG. 9, are isolated from all other fluid channels in testing unit 50, i.e., main infusion channel 120. Fluid communication between test chamber 15 and other fluid channels (i.e., main channel 120) is temporarily blocked. Forward pumping of the infusion fluid, with the balloons 81,82 deflated, as shown in FIG. 10, clears the test chamber 15 of blood.

As shown in FIG. 10, after the testing of the sample, first and second balloon valves are opened.

FIGS. 11-20 illustrate a second, preferred embodiment of the invention wherein the testing unit 250 includes a main infusion channel or passageway 320 and a novel side channel 420. The side channel 420 includes test chamber 215 having electrode 212. First and second balloon valves 281 and 282 are located in side channel 420 and are adjacent test chamber 215 and on opposite sides of test chamber 215. A third balloon valve 283 is located in main channel 320. Closing of third valve 283 causes infusion fluid and/or blood to flow through side channel 420. Side channel 420 is more restrictive in cross-sectional area than main channel 320 as described above. A fourth balloon valve 284 is located in calibration fluid channel 460; calibration fluid channel 460 is in fluid communication with side channel 420. Opening fourth valve 284 allows calibration fluid to enter side channel 420 and to flush test chamber 215 (with valves 281,282 open and valve 283 closed). Test chamber 215 has a volume between 8 μL and 12 μL and a cross-sectional height greater than 300 microns, as noted above.

Figure 11:
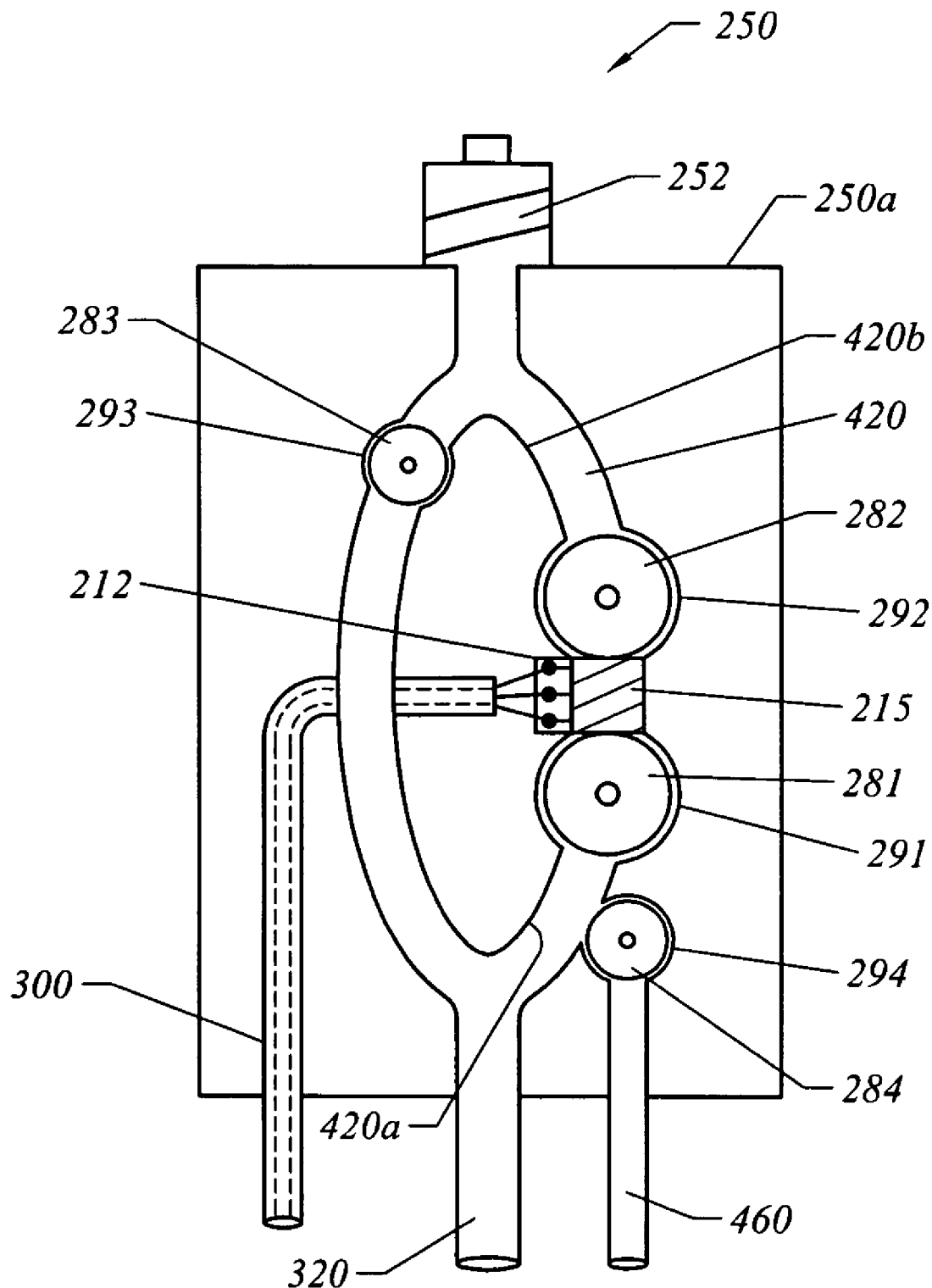
FIGS. 11-20 are schematic illustrations of the second, preferred embodiment of the invention, illustrating the steps of performing the glucose testing according to the invention.

FIG. 11 is a sagittal view along the central plane of a second version of the testing unit 250, drawn to its actual size, which is 2¼"×1½" by ¾". The connector 252 is permanently attached to the distal end 205a of the testing unit 250 and is in continuity with main infusion channel 320 and side channel 420. Inflatable balloon valves 281, 282, 283 and 284 rest in balloon chambers 291, 292, 293 and 294. Two narrow slits 420a and 420b, approximately 300 microns high, connect the proximal and distal ends of the side channel through the two balloon chambers 291 and 292. Glucose sensor 212 rests at the bottom of the test chamber 215 wherein the top of the sensor makes contact with fluid to be tested. Sensor 212 is connected by cable 300 to the electronics of the bedside monitor.

Figure 12:
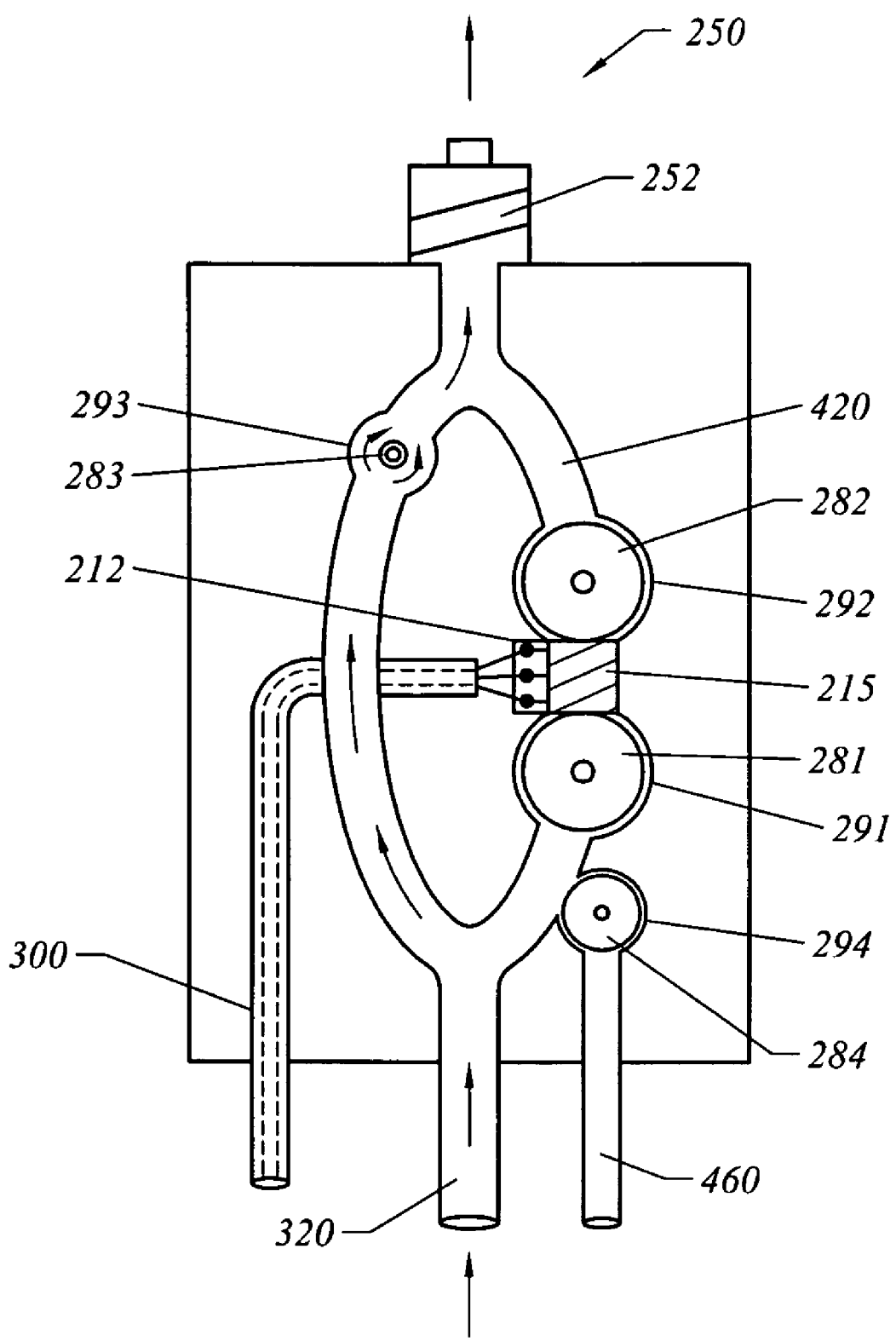

FIG. 12 is the same view as shown in FIG. 11, enlarged approximately 2×. All balloon valves (281, 282 and 284) except the main channel balloon 283 in the balloon chamber 293 are inflated, closing the valves. Normal flow of infusion fluid through the main channel 320 is shown in this drawing. Patient blood vessel catheter (not shown) is attached to luer connector 252.

Figure 13:
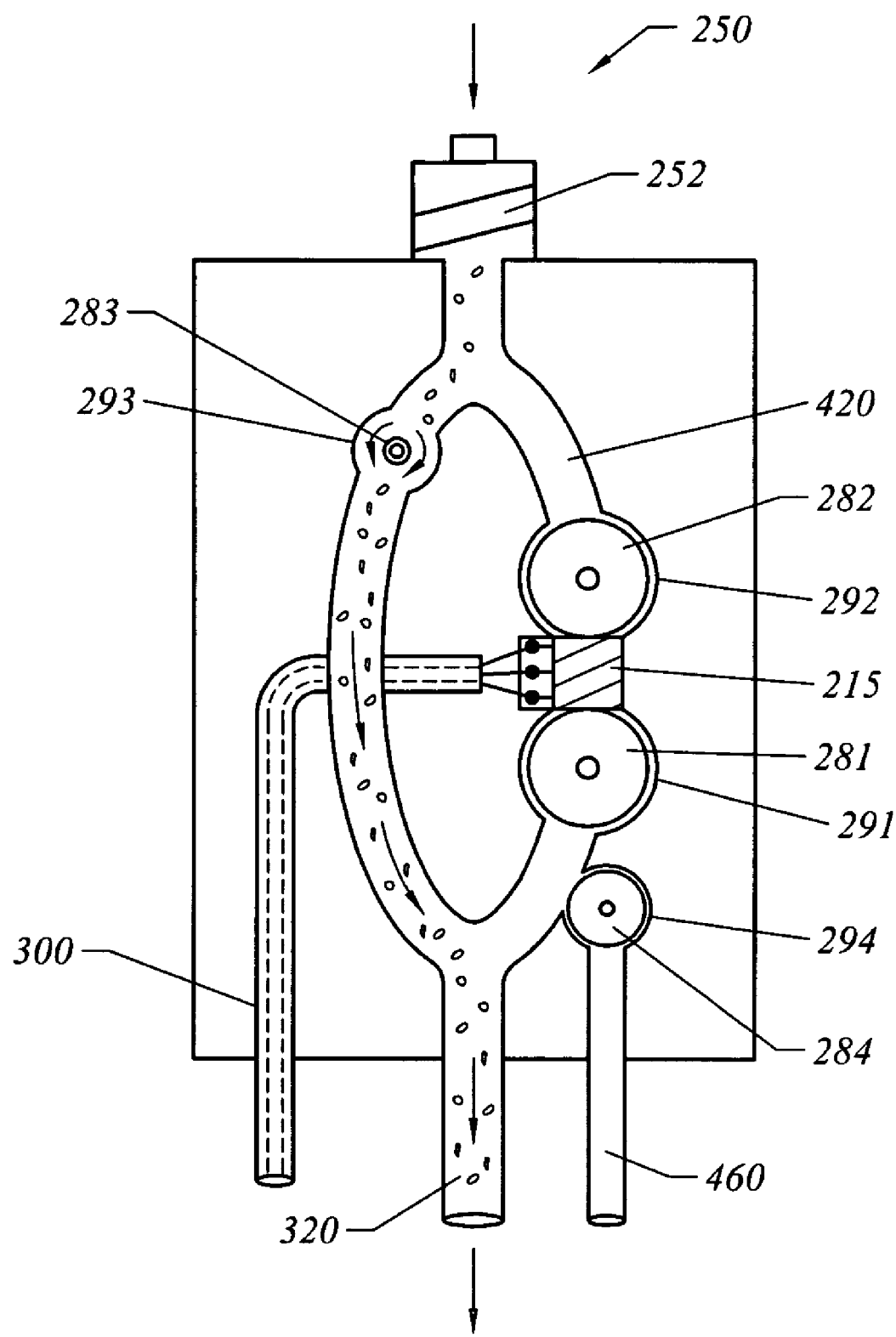

FIG. 13 shows blood being drawn from the patient by reversing the peristaltic pump. Reverse pumping is stopped when the optics (not shown) of the testing unit 250 indicate that undiluted blood is now in the test chamber 215.

Figure 14:
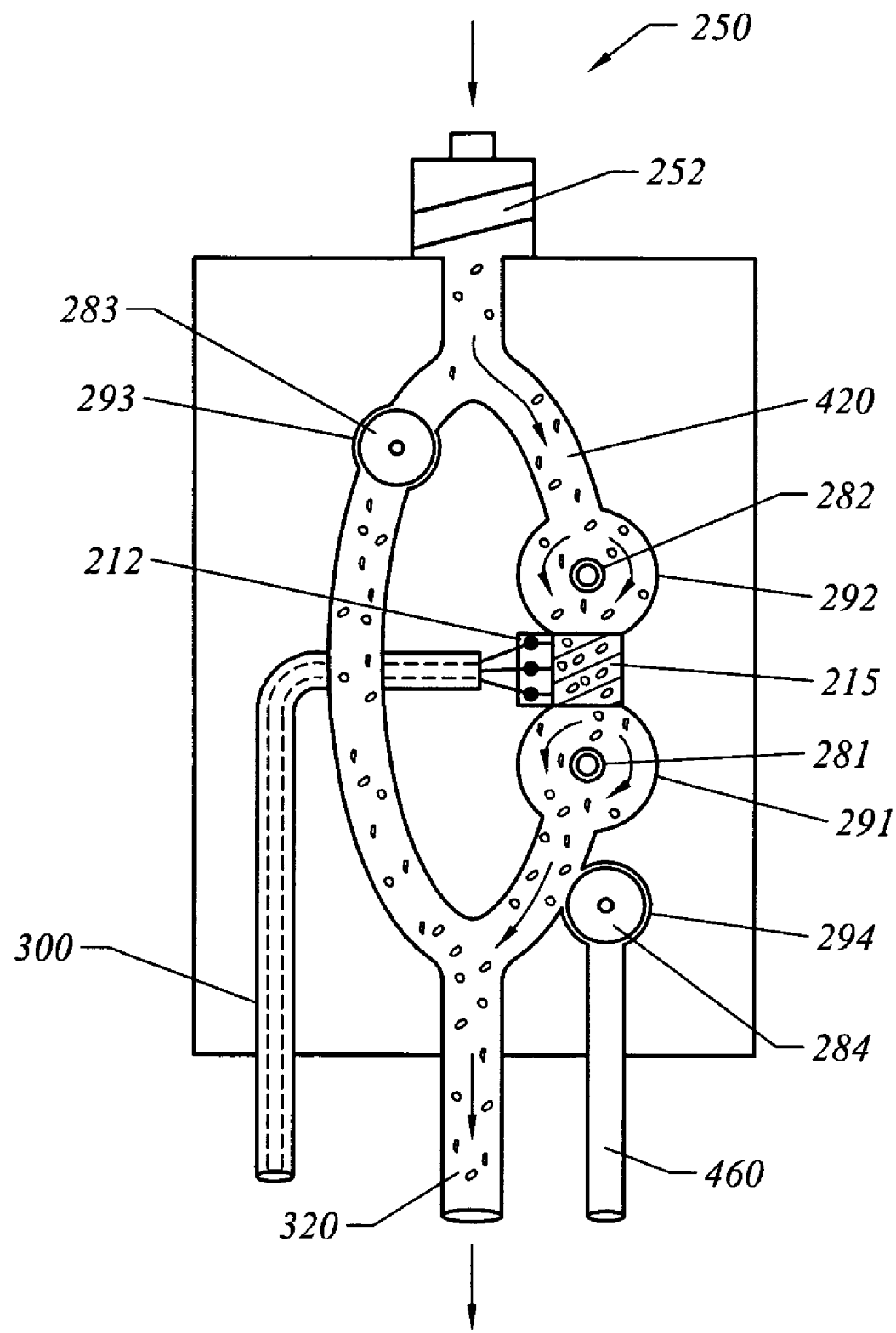

FIG. 14 shows the balloon 281 of the main channel 320 now completely inflated and closed. Reverse peristaltic pumping now draws blood into the side channel 420 and into the test chamber 215. It should be appreciated that a controllable valve 283 in the main channel 320 is an essential aspect of the invention. Without controlled blockage of the main channel, fluid could not be forced through the restricted side channel 420 and fluids would always take the path of least resistance through the main channel 320.

Figure 15:
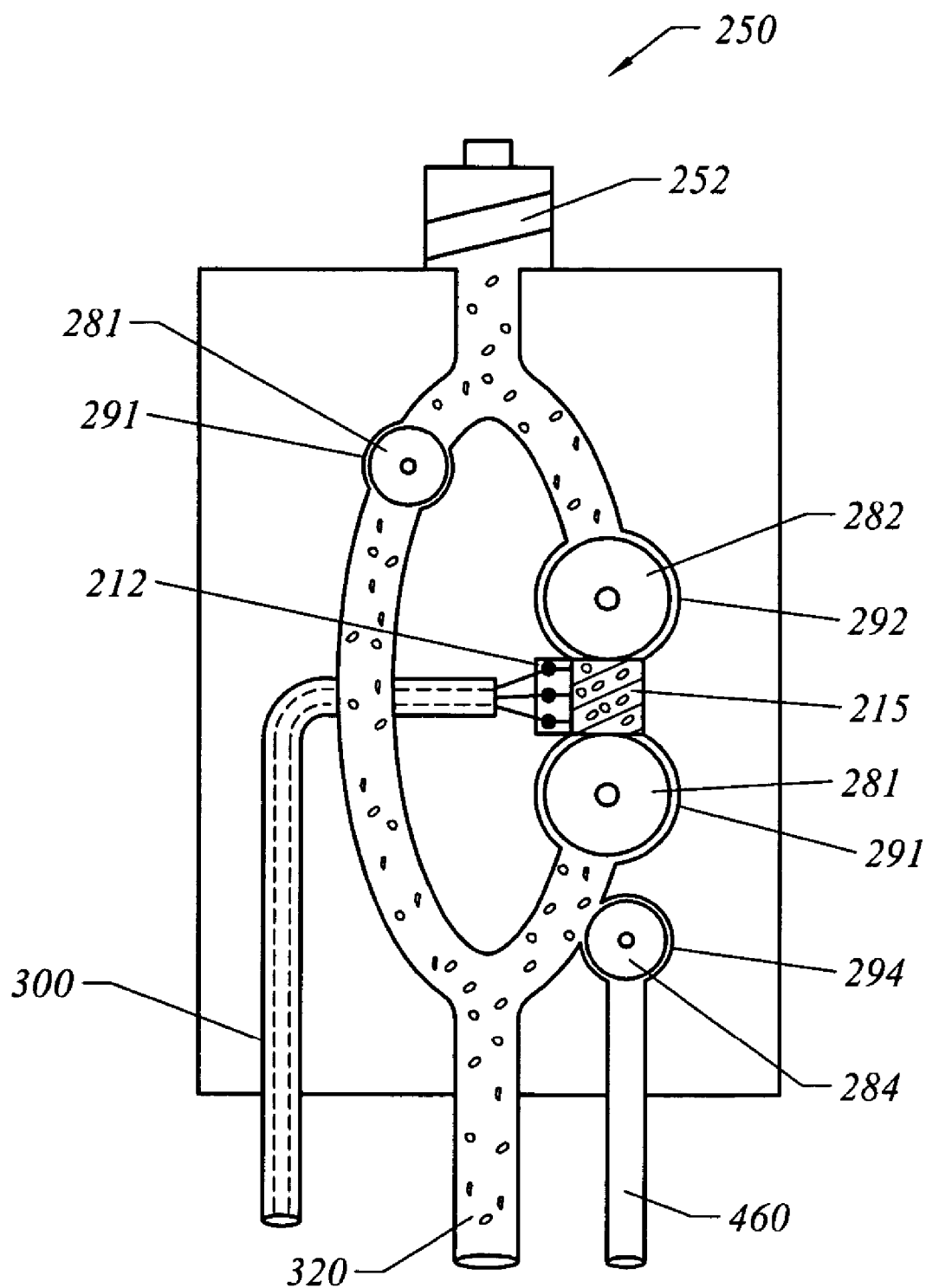

FIG. 15 shows all four balloons inflated and peristaltic pumping stopped for approximately 20 seconds while the blood in test chamber 215 over the sensor 212 is tested. Both entrances to the test chamber 215 are temporarily completely blocked by the inflated first and second balloons 281,282 so that the glucose diffusion gradient over the sensor 212 is not perturbed during the test. The test chamber 215 and the blood sample therein are isolated from other fluid channels in testing unit 250.

Figure 16:
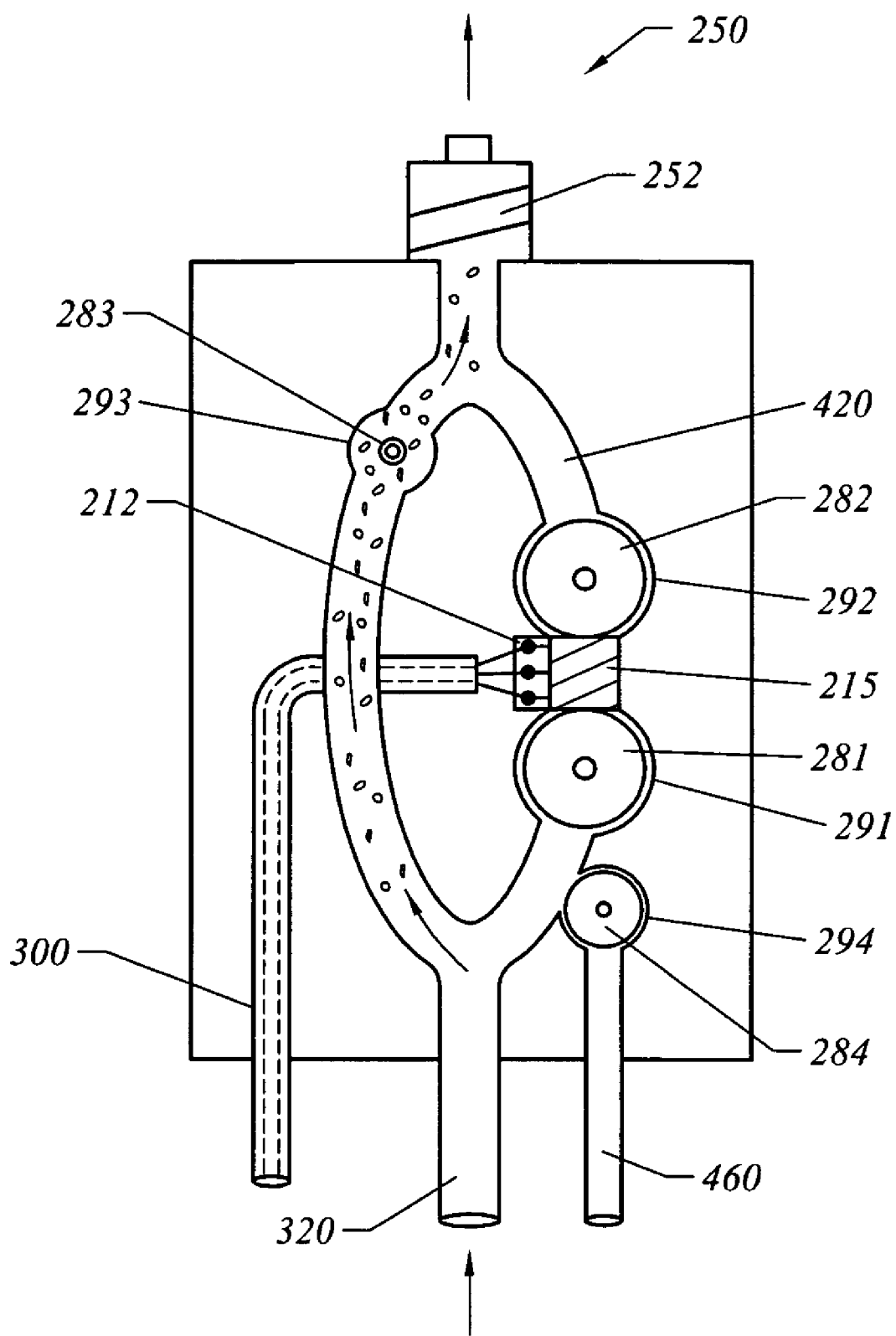

FIG. 16 shows the flushing of the main channel 320 shortly after the test has been performed in the test chamber 215 wherein the balloon valve 283 in the main channel is opened and infusion fluid is being pumped through the main channel toward the patient.

Figure 17:
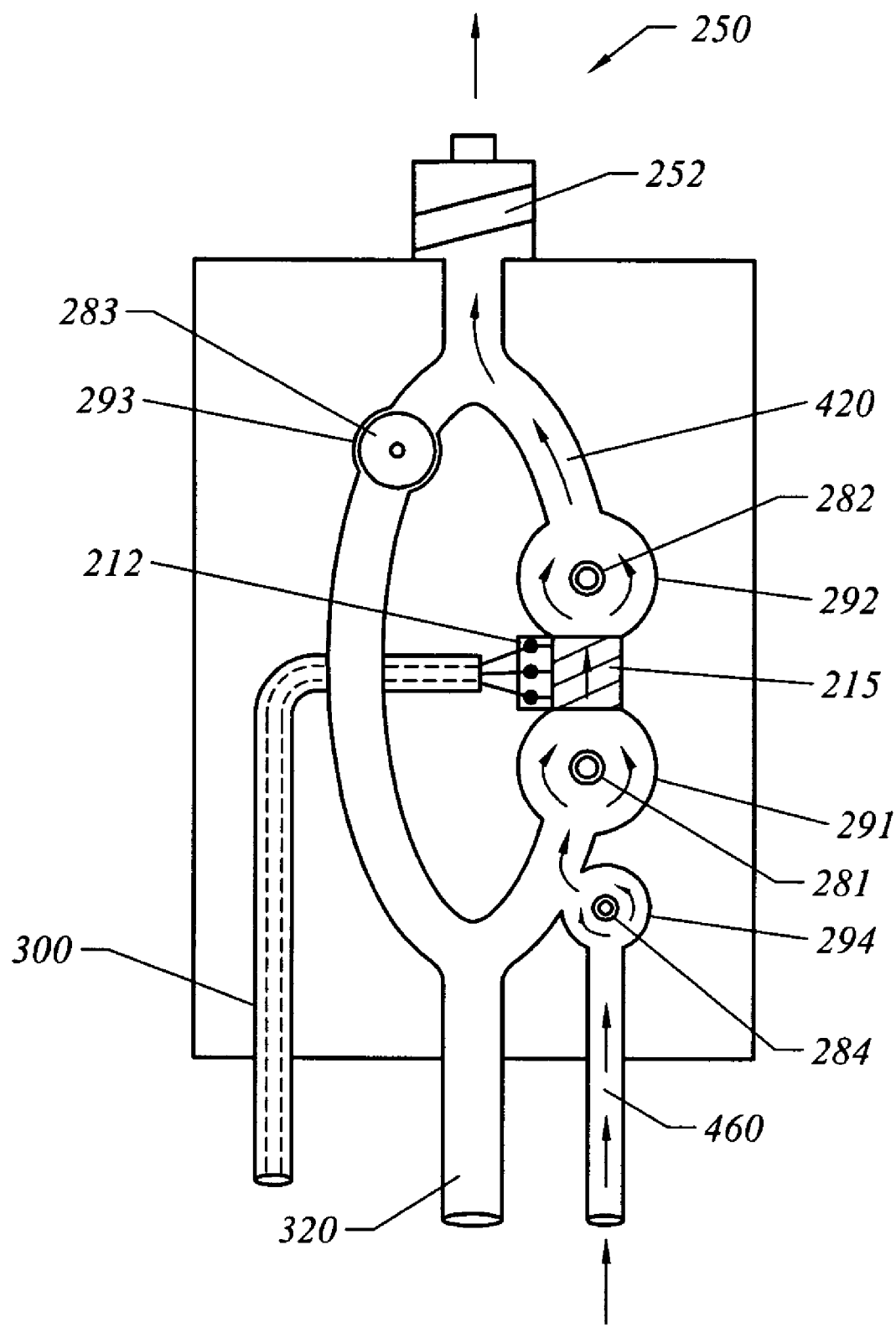

FIG. 17 illustrates the flushing or cleansing of the test chamber 215 with calibration fluid showing the valves 281,282 adjacent the test chamber 215 opened and the valve controlling calibration fluid opened and the valve 283 in the main infusion channel 320 is closed to force the calibration fluid to flow through and flush the test chamber.

Figure 18:
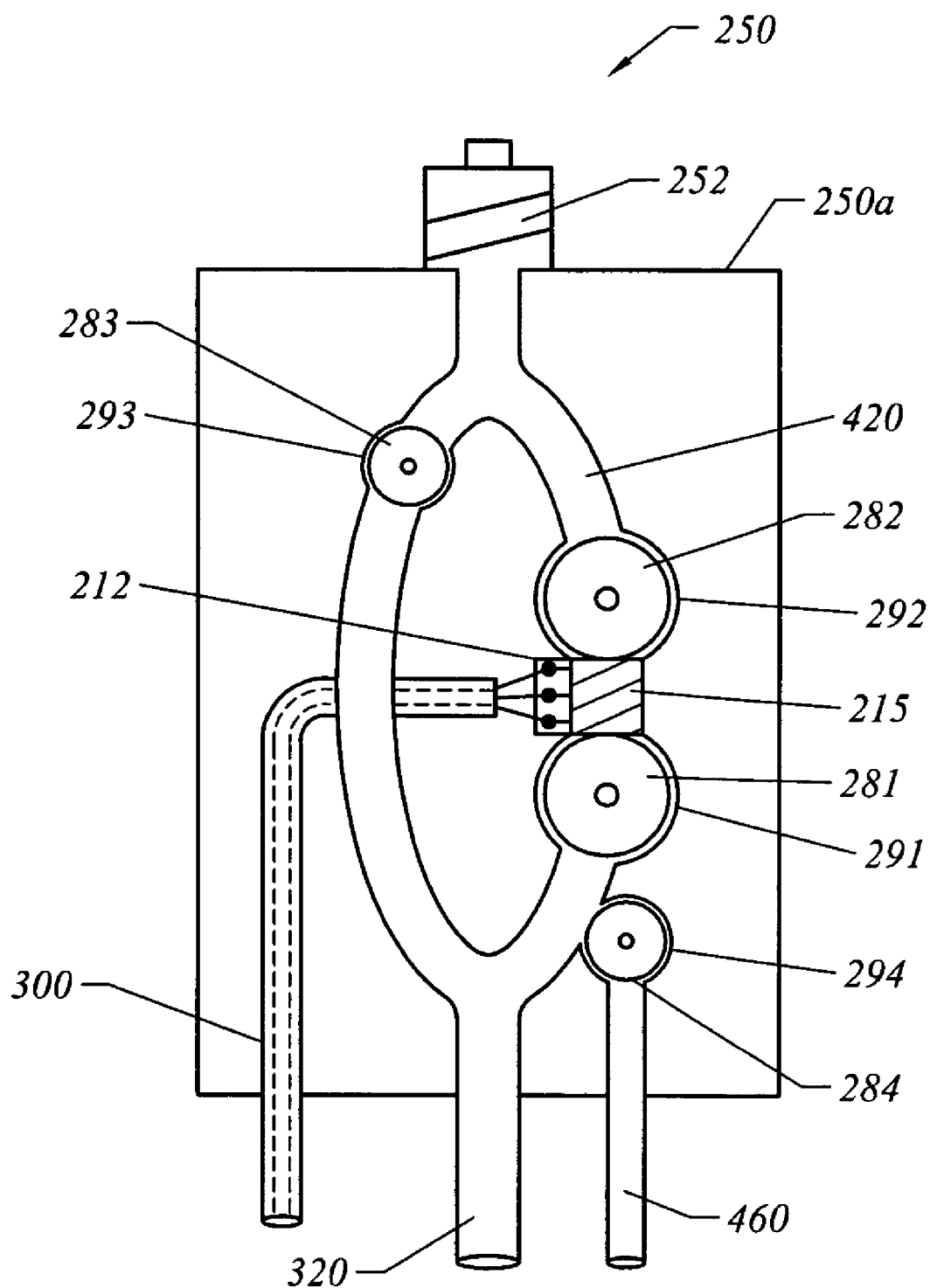

FIG. 18 illustrates all four balloon valves closed after the test chamber 215 has been flushed with calibration fluid, allowing the test chamber to be recalibrated.

Figure 19:
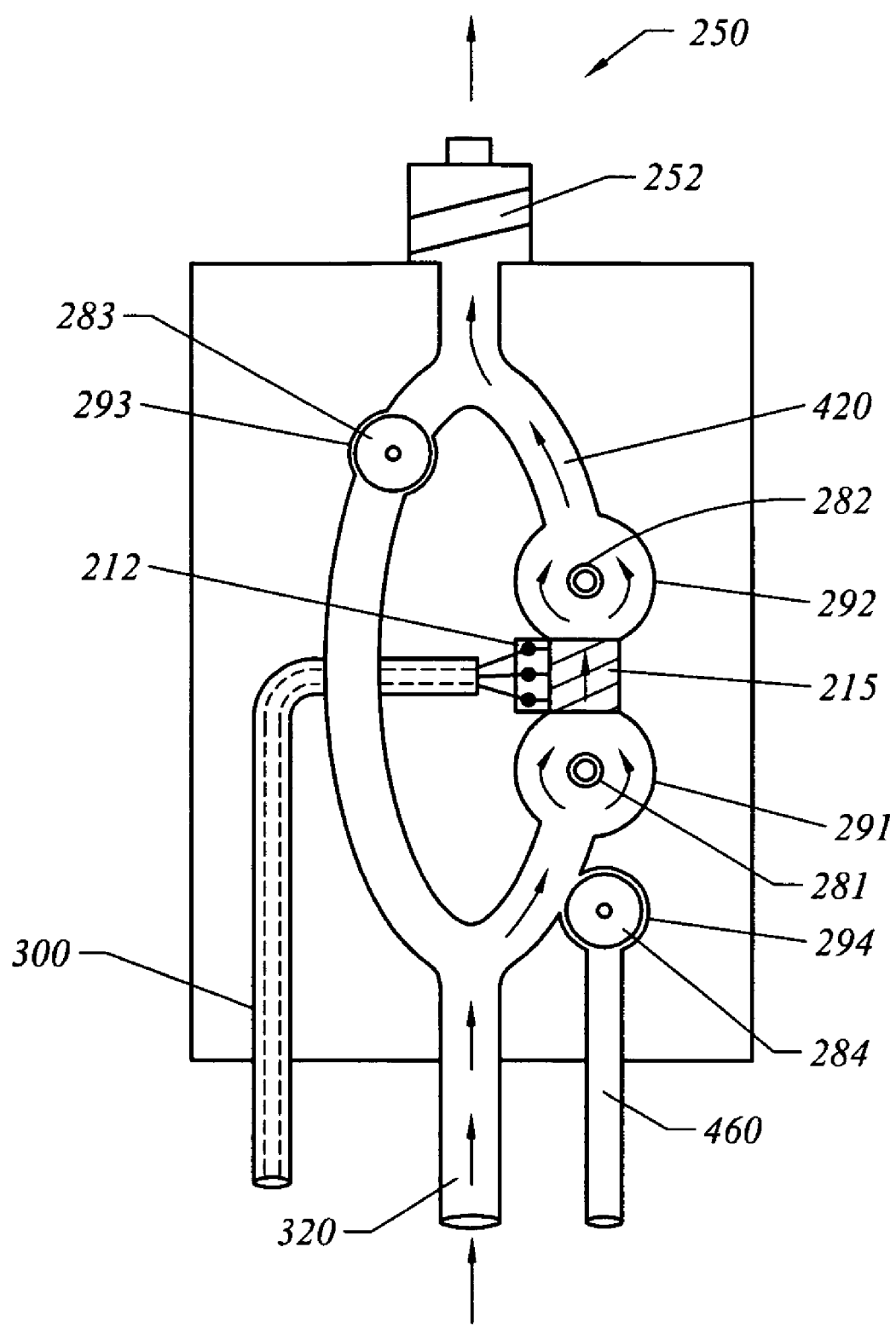

FIG. 19 illustrates the reintroduction of infusion fluid through the side channel 420 (with valves 281,282 open and valves 283,284 closed) after the calibration fluid has been pumped through the side channel for calibration purposes.

Figure 20:
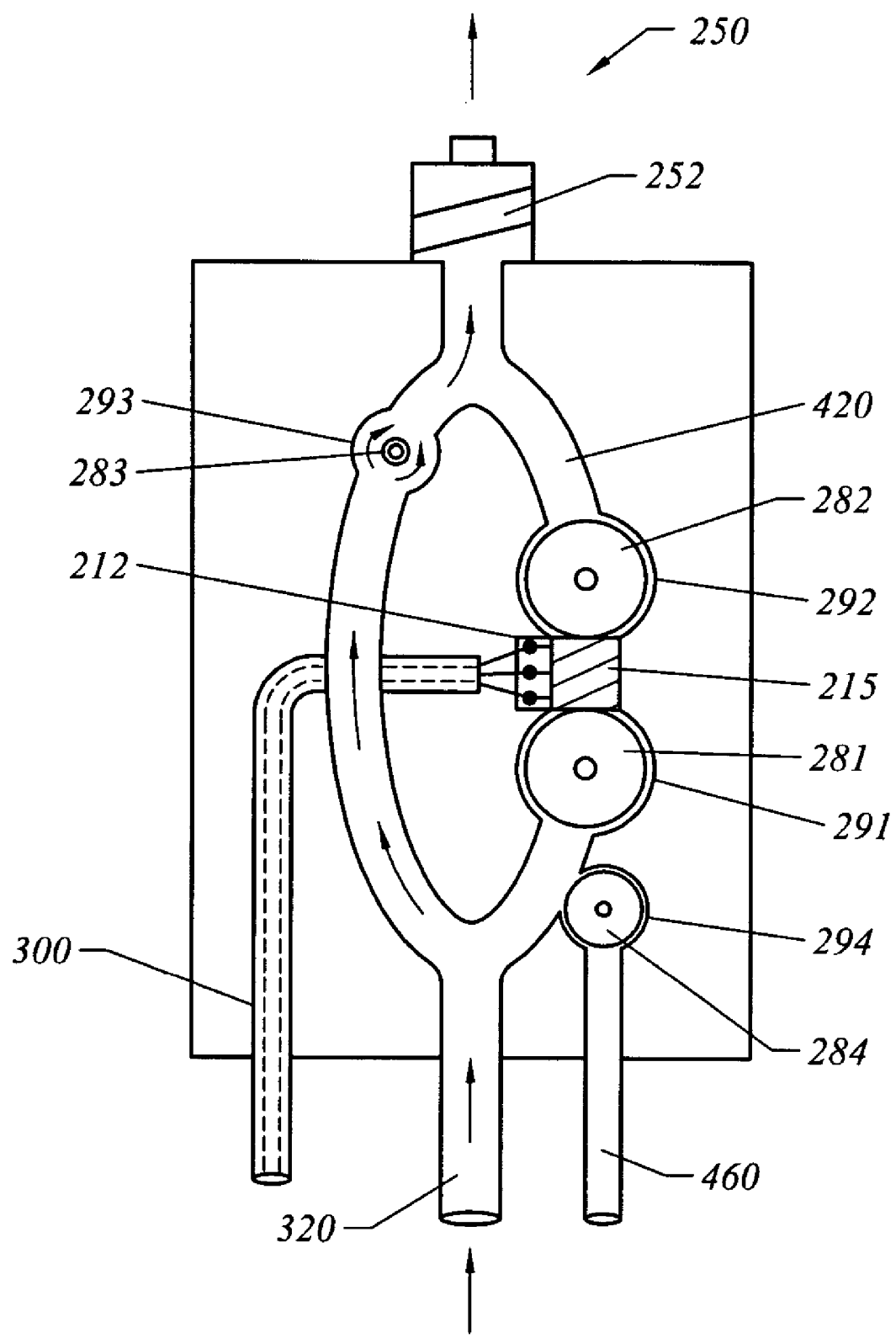

FIG. 20 illustrates reintroduction of infusion fluid through the main channel 320 (with valve 283 open, valves 281,282 and 284 closed).

FIGS. 21-25 illustrate a series of glucose consumption curves and illustrate the significance of utilizing the "stable diffusion gradient" of the present invention compared with prior art glucose consumption curves.

Figure 21:
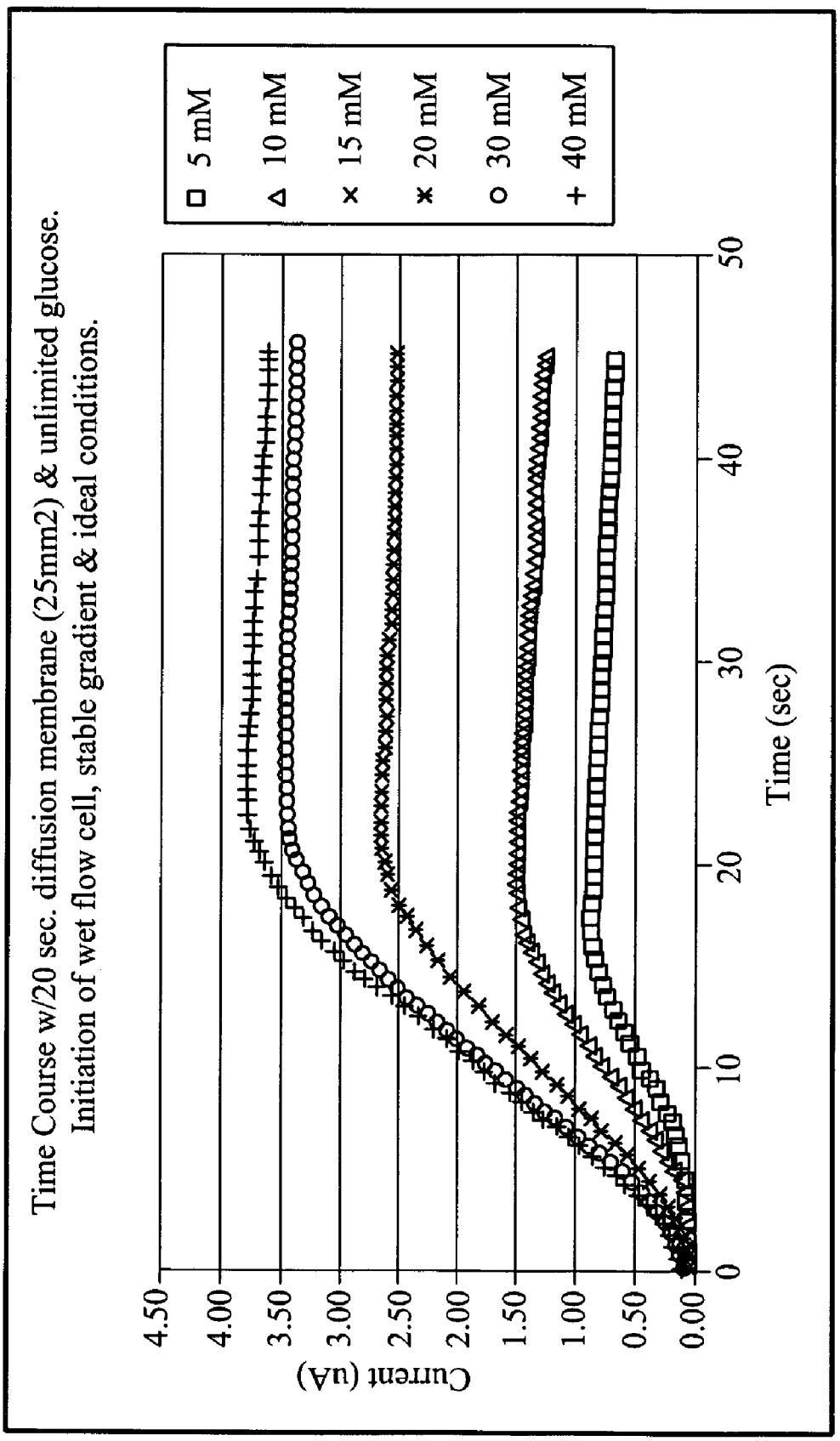
FIGS. 21-25 illustrate a series of glucose consumption curves and illustrate the significance of utilizing the "stable diffusion gradient" of the present invention compared with prior art glucose consumption curves.

FIG. 21 illustrates glucose consumption curves under ideal conditions utilizing a stabilized diffusion gradient according to the invention for five different blood glucose concentration levels.

Figure 22:
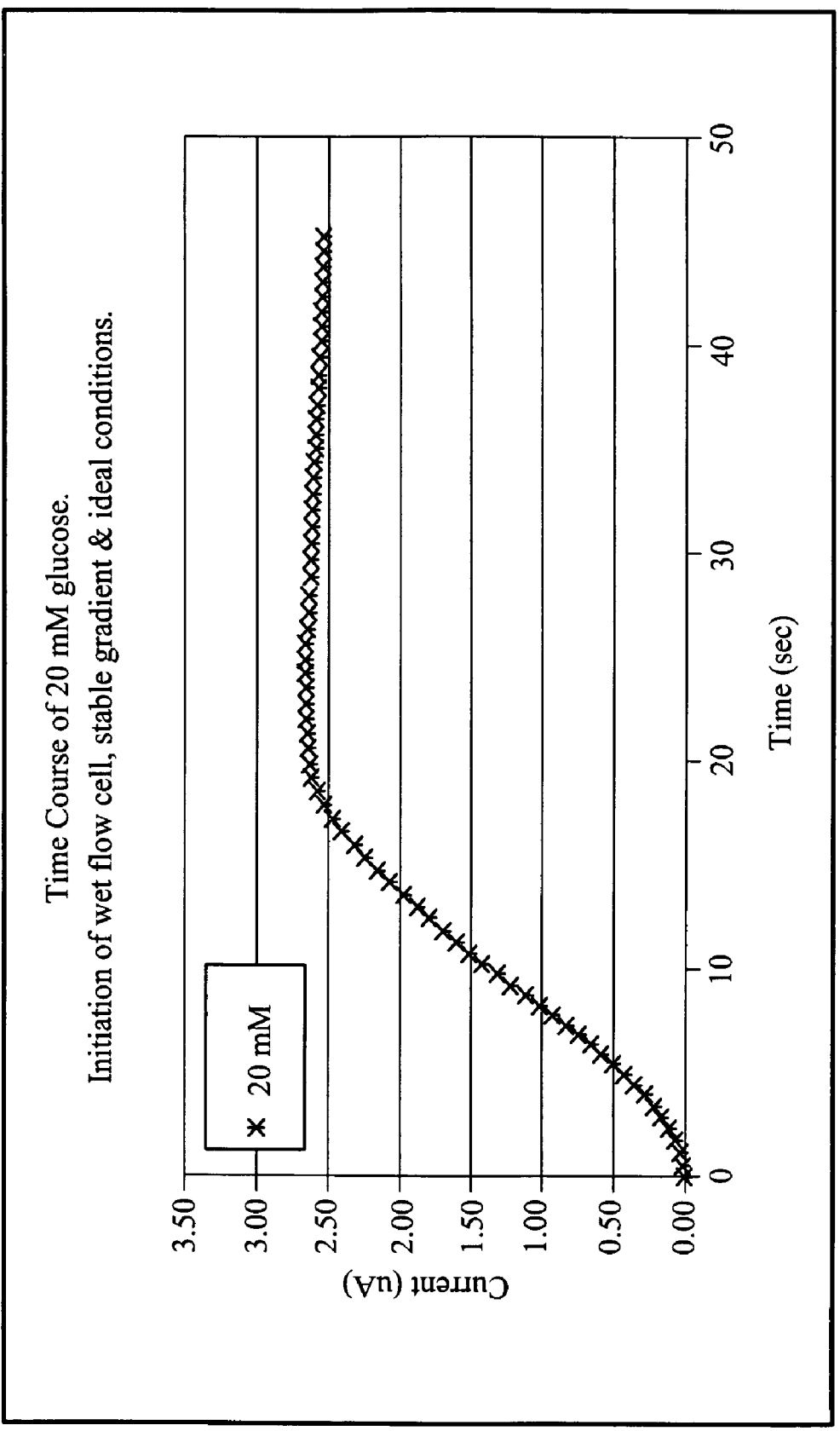

FIG. 22 is a glucose consumption curve (or current flow curve) utilizing the stable diffusion gradient technique of the present invention for one given blood glucose level.

Figure 23:
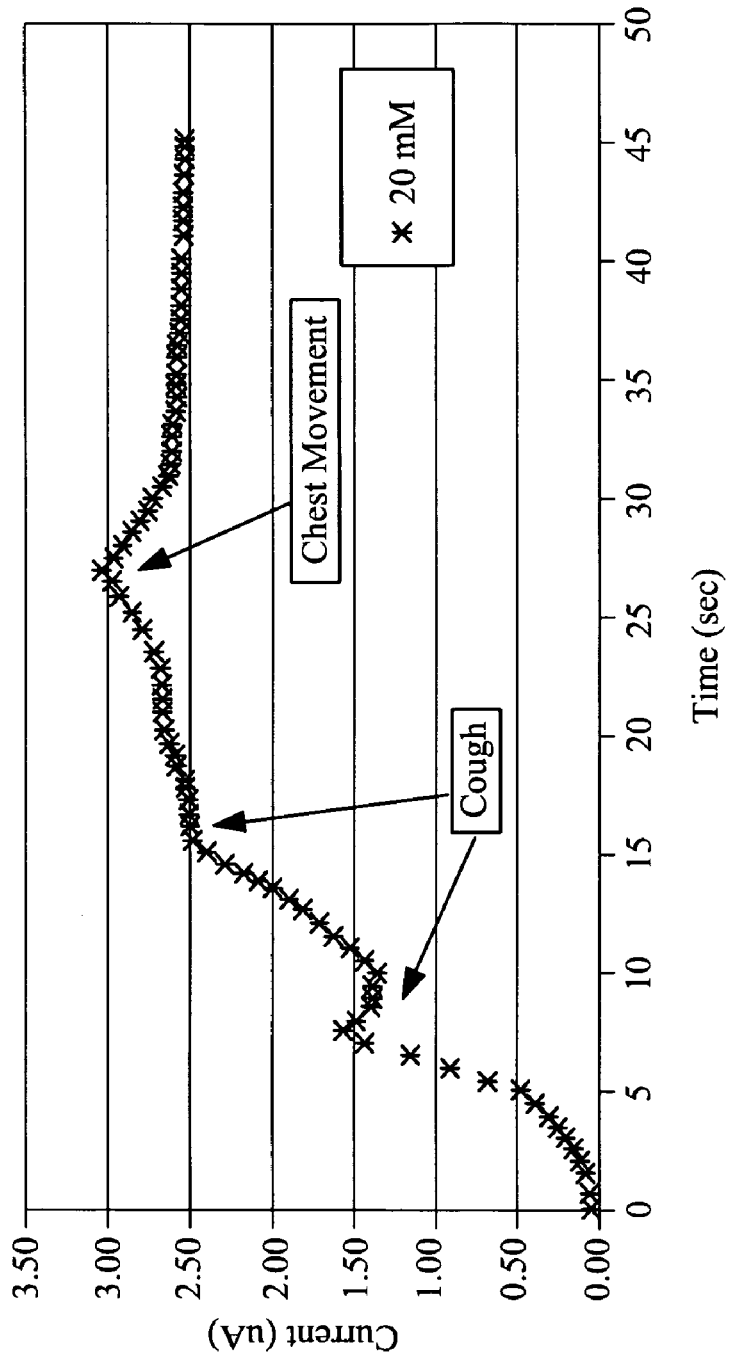

FIG. 23 illustrates a prior art glucose consumption curve wherein perturbations or disturbances caused by coughing or other chest motion of the patient will produce an erroneous blood glucose reading.

Figure 24:
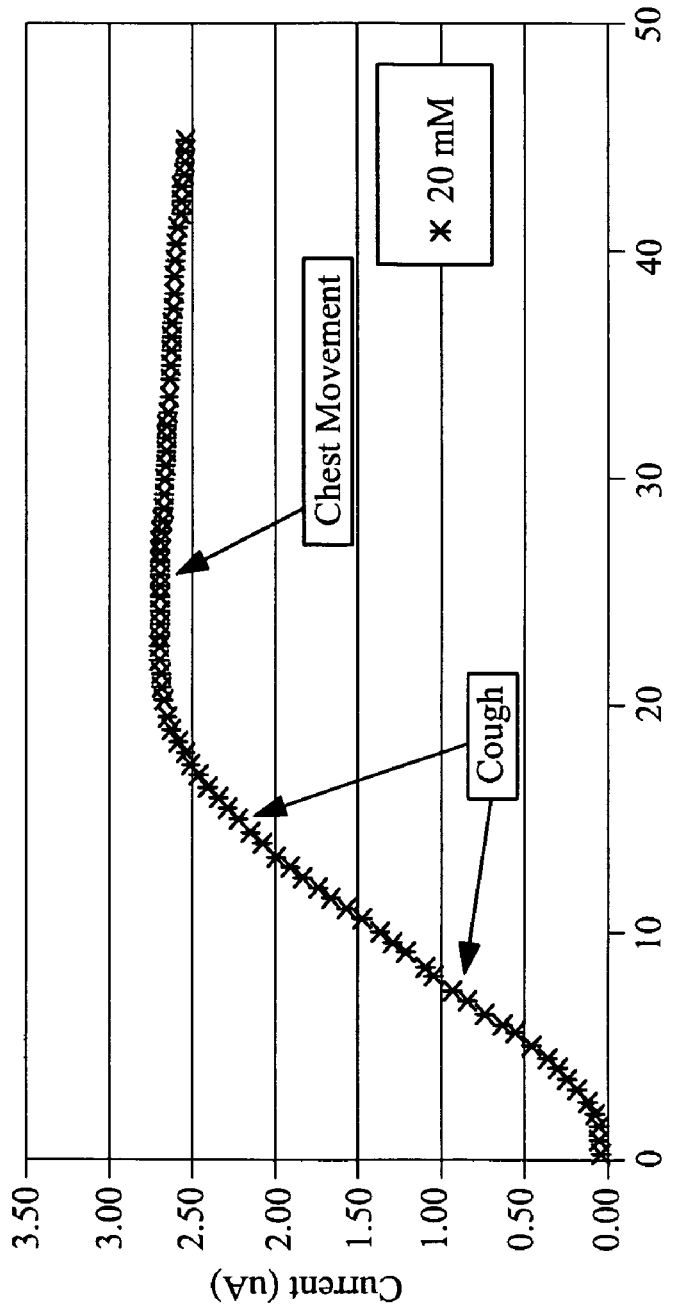

FIG. 24 illustrates a glucose consumption curve or current flow curve where the isolation techniques of the present invention are utilized and wherein coughing or chest motion of the patient has very little, if any, effect on the blood glucose measurement. Small and insignificant artifacts are sometimes seen, marking the points where much larger changes in the curve would occur without test chamber isolation.

Figure 25:
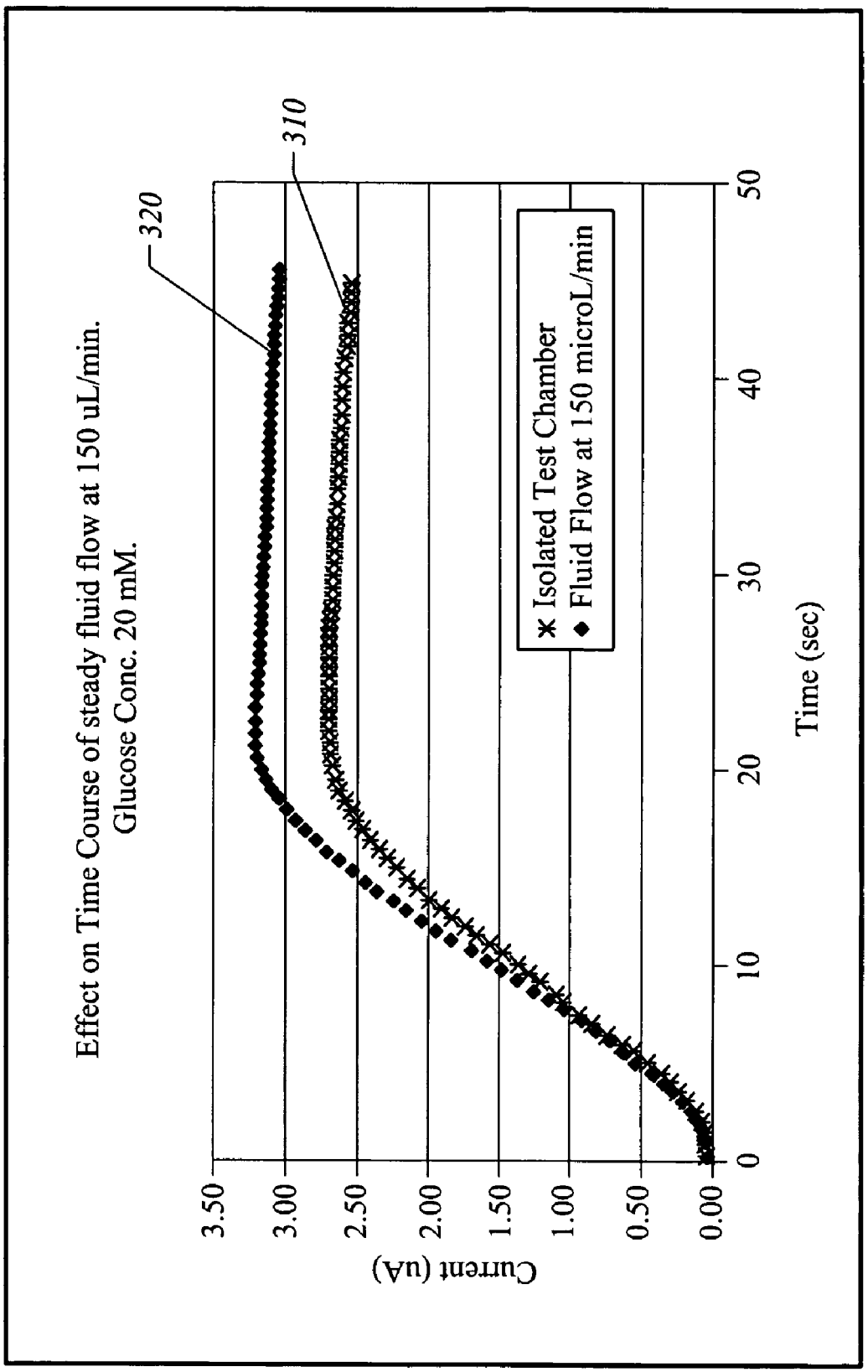

FIG. 25 illustrates a first glucose consumption curve 310 obtained by utilizing the isolated test chamber of the present invention. FIG. 25 also includes a second glucose consumption curve 320 that is obtained if the test chamber is not isolated according to the present invention, but where a very slow flow rate of 150 µL/minute of fluid is allowed to pass into or through the test chamber during a test. The second curve 320 results in a 20% overestimation of glucose concentration.

Figure 26:
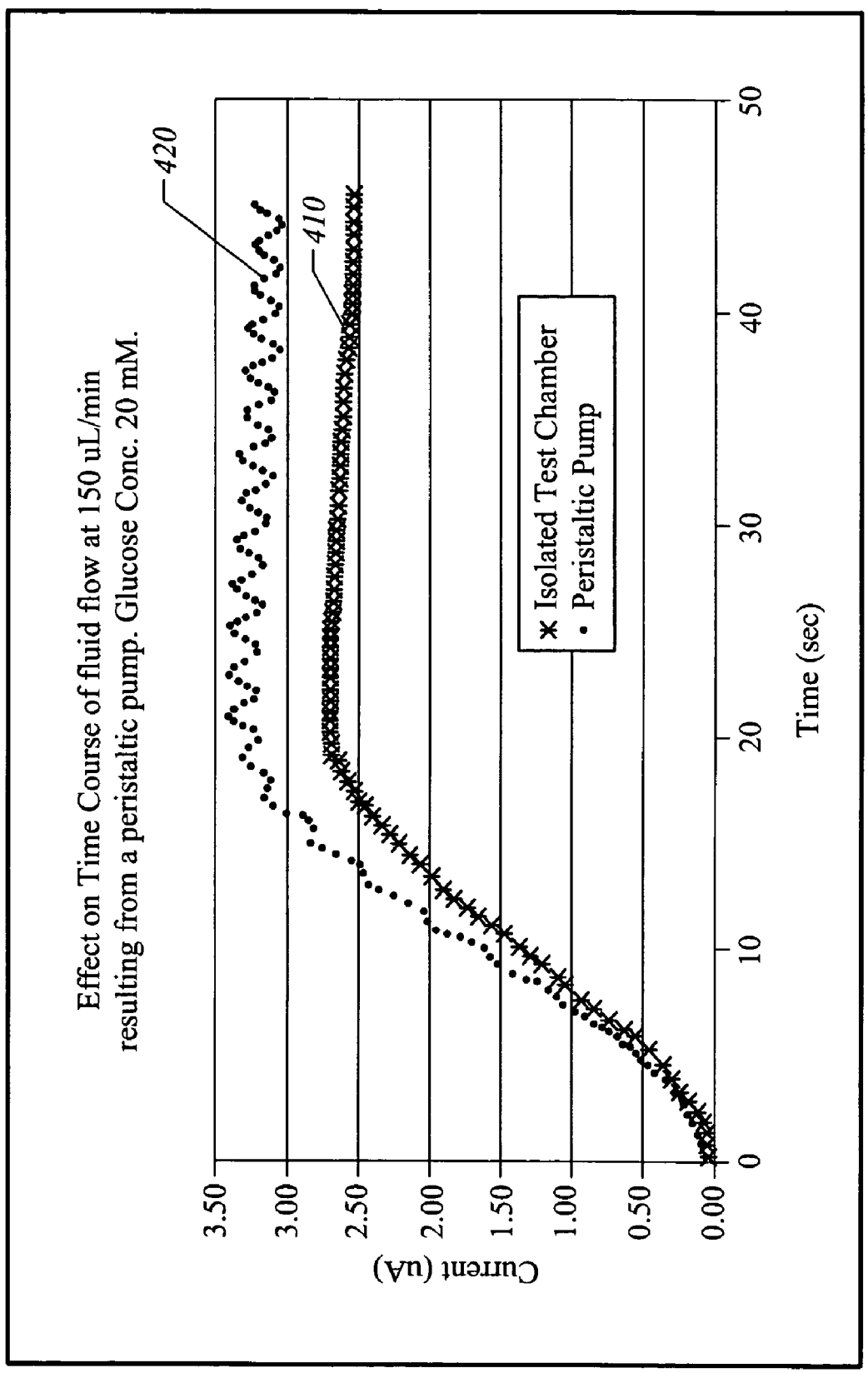
FIG. 26 is a pair of glucose consumption curves illustrating how a slow flow rate of blood pumped through a non-isolated prior art test chamber by a peristaltic pump will produce a varying and erroneously high blood glucose measurement.

FIG. 26 illustrates a first glucose consumption curve 410 obtained by utilizing the isolated test chamber of the present invention. FIG. 26 also includes a second glucose consumption curve 420 obtained if the test chamber is not isolated according to the present invention, but where a peristaltic pump is slowly pumping fluid at 150 µL/minute into or through the test chamber. Curve 420 illustrates the "cog wheel" or pulsating effect of such a pump. Curve 420 also illustrates how erroneously high blood glucose measurements are obtained if the test sample is not isolated and small amounts of fluid are allowed to be slowly pumped into or through the test chamber during a test. The glucose measurement induced by 150 µL/minute flow is approximately 20% higher than the correct value due to disruption of the diffusion gradient.

The foregoing description of the invention has been presented for purposes of illustration and description and is not intended to be exhaustive or to limit the invention to the precise form disclosed. Modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. An apparatus for automatically and periodically measuring a patient's blood glucose level comprising:
   a testing unit,
   infusion lines to connect said testing unit to a source of infusion fluid and to a catheter placed in a patient's blood vessel,
   reversible peristaltic pump means to move infusion fluid or blood either forwardly through said testing unit into said blood vessel catheter or backwardly into said testing unit and said infusion line,
   a main channel for blood or infusion fluid within said testing unit,
   a side channel in the testing unit connected to said main channel,
   a test chamber within said side channel for glucose testing, and
   valve means for controlling fluid flow through said main channel and isolating said test chamber in said side channel, wherein said valve means includes first and second valves in said side channel for isolating a blood sample in said test chamber, said first and second valves being adjacent to and on opposite sides of said test chamber, further comprising third valve means in said main channel for diverting fluid flow into said side channel, further comprising a calibration fluid channel in fluid communication with said side channel and fourth valve means in said calibration fluid channel to allow calibration fluid to flow through said side channel and said test chamber, wherein each of said valve means is a balloon valve.

* * * * *